(12) United States Patent
Hattori et al.

(10) Patent No.: US 12,115,021 B2
(45) Date of Patent: Oct. 15, 2024

(54) ULTRASOUND SYSTEM AND METHOD OF CONTROLLING ULTRASOUND SYSTEM

(71) Applicant: FUJIFILM Corporation, Tokyo (JP)

(72) Inventors: Masato Hattori, Kanagawa (JP); Keiji Tsubota, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/572,672

(22) Filed: Jan. 11, 2022

(65) Prior Publication Data

US 2022/0125409 A1 Apr. 28, 2022

Related U.S. Application Data

(63) Continuation of application No. PCT/JP2020/029424, filed on Jul. 31, 2020.

(30) Foreign Application Priority Data

Aug. 15, 2019 (JP) ................................. 2019-149088

(51) Int. Cl.
*A61B 8/00* (2006.01)
*A61B 8/08* (2006.01)
*G16H 40/67* (2018.01)

(52) U.S. Cl.
CPC .......... *A61B 8/4494* (2013.01); *A61B 8/4472* (2013.01); *A61B 8/4488* (2013.01);
(Continued)

(58) Field of Classification Search
CPC ... A61B 8/4472; A61B 8/4488; A61B 8/4494; A61B 8/461; A61B 8/463; A61B 8/465;
(Continued)

(56) References Cited

U.S. PATENT DOCUMENTS

2002/0087080 A1* 7/2002 Slayton .................... A61B 8/42
600/459
2015/0164479 A1* 6/2015 Toji ........................ A61B 8/463
600/440

(Continued)

FOREIGN PATENT DOCUMENTS

CN 108289613 A 7/2018
JP 2008302146 A * 12/2008
(Continued)

OTHER PUBLICATIONS

Translated Foreign Tsuchiya JP 200802146 A (Year: 2008).*
(Continued)

*Primary Examiner* — Joseph M Santos Rodriguez
*Assistant Examiner* — Brooke Lyn Klein
(74) *Attorney, Agent, or Firm* — Studebaker & Brackett PC

(57) ABSTRACT

An ultrasound system (1) includes an ultrasound probe (2), a mobile information terminal (3), and an external apparatus (4). The ultrasound probe (2) includes a transmission and reception circuit (22) that transmits an ultrasonic wave from a transducer array (21) and generates a sound ray signal, and a reception data generation unit that generates reception data before imaging based on the sound ray signal. The mobile information terminal (3) includes a camera unit (33) that acquires a view image. The external apparatus (4) includes a display controller (44) that displays an ultrasound image generated based on the reception data and the view image on an external monitor (45), and an input device (47). In a case where a probe freeze instruction is input from the input device (47), the transmission of the ultrasonic wave from the transducer array (21) is stopped.

17 Claims, 17 Drawing Sheets

(52) U.S. Cl.
    CPC .............. *A61B 8/461* (2013.01); *A61B 8/463* (2013.01); *A61B 8/467* (2013.01); *A61B 8/5207* (2013.01); *A61B 8/54* (2013.01); *A61B 8/565* (2013.01); *G16H 40/67* (2018.01)

(58) Field of Classification Search
    CPC ......... A61B 8/467; A61B 8/5207; A61B 8/54; A61B 8/565; G16H 40/67
    See application file for complete search history.

(56) References Cited

U.S. PATENT DOCUMENTS

| | | | |
|---|---|---|---|
| 2016/0100824 A1* | 4/2016 | Kim ...................... | A61B 8/461 600/437 |
| 2017/0049419 A1* | 2/2017 | Park ..................... | A61B 8/5207 |
| 2017/0112439 A1 | 4/2017 | Dubin et al. | |
| 2019/0038260 A1* | 2/2019 | Lee ......................... | A61B 8/00 |

FOREIGN PATENT DOCUMENTS

| | | | |
|---|---|---|---|
| JP | 2011-087729 A | 5/2011 | |
| JP | 2011-183056 A | 9/2011 | |
| JP | 2015-053957 A | 3/2015 | |
| JP | 2017-086360 A | 5/2017 | |
| WO | 2015/037510 A1 | 3/2015 | |

OTHER PUBLICATIONS

An Office Action; "Notice of Reasons for Refusal," mailed by the Japanese Patent Office on Feb. 7, 2023, which corresponds to Japanese Patent Application No. 2021-539205 and is related to U.S. Appl. No. 17/572,672; with English language translation.

International Search Report issued in PCT/JP2020/029424; mailed Oct. 13, 2020.

International Preliminary Report on Patentability and Written Opinion issued in PCT/JP2020/029424 issued Feb. 8, 222.

"Notice of Reasons for Refusal" Office Action issued in JP 2021-539205; mailed by the Japanese Patent Office on Jul. 18, 2023.

The Extended European Search Report issued by the European Patent Office on Aug. 26, 2022, which corresponds to European Patent Application No. 20851688.0-1126 and is related to U.S. Appl. No. 17/572,672.

An Office Action mailed by China National Intellectual Property Administration on Aug. 18, 2023, which corresponds to Chinese Patent Application No. 202080057401.4 and is related to U.S. Appl. No. 17/572,672; with English translation.

An Office Action mailed by China National Intellecutal Property Administration on Apr. 19, 2024, which corresponds to Chinese Patent Application No. 202080057401.4 and is related to U.S. Appl. No. 17/572,672; with English language translation.

* cited by examiner

ULTRASOUND SYSTEM AND METHOD OF CONTROLLING ULTRASOUND SYSTEM

CROSS-REFERENCE TO RELATED APPLICATIONS

This application is a Continuation of PCT International Application No. PCT/JP2020/029424 filed on Jul. 31, 2020, which claims priority under 35 U.S.C. § 119(a) to Japanese Patent Application No. 2019-149088 filed on Aug. 15, 2019. The above application is hereby expressly incorporated by reference, in its entirety, into the present application.

BACKGROUND OF THE INVENTION

1. Field of the Invention

The present invention relates to an ultrasound system and a method of controlling an ultrasound system, and in particular, to an ultrasound system that displays an ultrasound image on a mobile information terminal and a method of controlling an ultrasound system.

2. Description of the Related Art

Hitherto, in a medical field, an ultrasound diagnostic apparatus using an ultrasound image has come into practical use. In general, this kind of ultrasound diagnostic apparatus has an ultrasound probe that incorporates a transducer array, and an apparatus body connected to the ultrasound probe. The ultrasound probe transmits ultrasonic waves toward a subject and receives ultrasound echoes from the subject, and the apparatus body electrically processes reception signals to generate an ultrasound image.

In recent years, for example, as disclosed in JP2017-86360A, an ultrasound diagnostic apparatus has been developed that displays an ultrasound image acquired using an ultrasound probe on an external monitor disposed at a position away from a user, and comprises a mobile information terminal for performing an input operation of the ultrasound probe and the external monitor, thereby improving convenience in ultrasound diagnosis.

SUMMARY OF THE INVENTION

In general, it is known that, in ultrasound diagnosis using an ultrasound diagnostic apparatus as disclosed in JP2017-86360A, a given level or higher of skill is needed to accurately recognize a part in a subject rendered in an ultrasound image by confirming the ultrasound image. Furthermore, it is known that the image quality of the generated ultrasound image significantly depends on the skill involving the hands of an operator.

Here, for example, in a case where an ultrasound image is captured at a remote location other than a hospital, such as home care, an operator who operates an ultrasound probe to capture an ultrasound image may be different from an observer who observes the captured ultrasound image to perform diagnosis.

In this case, since the operator normally needs to operate the ultrasound probe to capture an ultrasound image of an intended part in a subject while confirming the obtained ultrasound image personally, in particular, in a case where the level of skill of the operator is low, the operator may hardly determine whether or not the intended part of the subject is accurately observed. The operator having a low level of skill may not operate the ultrasound probe using appropriate skill involving the hands, and an ultrasound image with low image quality is obtained. The observer confirms the ultrasound image captured by the operator of the ultrasound diagnostic apparatus to perform diagnosis; however, since the observer cannot recognize a state in which the operator captures the ultrasound image, in particular, in a case where the ultrasound image is captured by the operator having a low level of skill, the observer may hardly accurately determine whether or not the captured ultrasound image is captured by appropriate skill involving the hands.

The present invention has been accomplished to solve such a problem in the related art, and an object of the present invention is to provide an ultrasound system and a method of controlling an ultrasound system capable of obtaining an appropriate ultrasound image and improving accuracy of ultrasound diagnosis even in a case where an ultrasound image is captured at a remote location.

To achieve the above-described object, there is provided a first ultrasound system according to the present invention that is an ultrasound system comprising an ultrasound probe, a mobile information terminal, and an external apparatus, in which the ultrasound probe includes a transducer array, a transmission and reception circuit that transmits an ultrasonic wave from the transducer array and generates a sound ray signal based on a reception signal acquired by the transducer array, an ultrasound image generation unit that generates an ultrasound image based on the sound ray signal generated by the transmission and reception circuit, and a probe-side wireless communication unit that wirelessly transmits the ultrasound image, the mobile information terminal includes a camera unit that acquires a view image obtained by imaging a scanning point of the ultrasound probe in a subject, and a terminal-side wireless communication unit that wirelessly transmits the view image acquired by the camera unit, the external apparatus includes an external wireless communication unit that is wirelessly connected to at least the terminal-side wireless communication unit, an external monitor, a display controller that displays the ultrasound image wirelessly transmitted from the ultrasound probe and the view image wirelessly transmitted from the mobile information terminal on the external monitor, and an external input device, and in a case where a probe freeze instruction is input from the external input device, the probe freeze instruction is transmitted from the external wireless communication unit and the transmission of the ultrasonic wave from the transducer array by the transmission and reception circuit of the ultrasound probe is stopped.

It is preferable that, in a case where the probe freeze instruction is input from the external input device, the probe freeze instruction is transmitted from the external wireless communication unit to the probe-side wireless communication unit through the terminal-side wireless communication unit.

In this case, it is preferable that, in a case where the probe freeze instruction is input from the external input device, the acquisition of the view image by the camera unit of the mobile information terminal is stopped.

In a case where the probe freeze instruction is input from the external input device, the probe freeze instruction may be transmitted from the external wireless communication unit to the probe-side wireless communication unit.

The external wireless communication unit may be wirelessly connected to both the probe-side wireless communication unit and the terminal-side wireless communication unit, and the probe-side wireless communication unit may wirelessly transmit the ultrasound image to both the mobile information terminal and the external apparatus.

The probe-side wireless communication unit may wirelessly transmit the ultrasound image to the mobile information terminal, and, and the terminal-side wireless communication unit may wirelessly transmit the ultrasound image wirelessly transmitted from the probe-side wireless communication unit and the view image acquired by the camera unit to the external apparatus.

The external monitor may include a microphone, and the stop of the transmission of the ultrasonic wave from the transducer array may be released by voice input through the microphone.

The external apparatus may include an image synchronization unit that synchronizes the ultrasound image and the view image with each other.

In this case, the external apparatus may include an image memory that stores the ultrasound image and the view image synchronized with each other by the image synchronization unit each time the probe freeze instruction is input from the external input device, and a thumbnail image generation unit that generate a plurality of thumbnail images each consisting of the ultrasound image and the view image stored in the image memory and displays the plurality of generated thumbnail images in a list on the external monitor.

The mobile information terminal may include a terminal monitor, and the ultrasound image and the view image may be displayed on the terminal monitor.

In this case, the mobile information terminal may include a terminal input device, and in a case where the probe freeze instruction is input from the external input device or the terminal input device, guidance on the probe freeze instruction may be displayed on the external monitor and the terminal monitor.

The external input device may have a touch sensor disposed on the external monitor in a superimposed manner, the terminal input device may have a touch sensor disposed on the terminal monitor in a superimposed manner, and in a case where the probe freeze instruction is input from the external input device or the terminal input device, as any one of a release button displayed on the external monitor, display for guidance on the probe freeze instruction displayed on the external monitor, a release button displayed on the terminal monitor, or display for guidance on the probe freeze instruction displayed on the terminal monitor may be touched, the stop of the transmission of the ultrasonic wave from the transducer array may be released.

The mobile information terminal may include a microphone, and the stop of the transmission of the ultrasonic wave from the transducer array may be released by voice input through the microphone.

The mobile information terminal may include an image synchronization unit that synchronizes the ultrasound image and the view image with each other.

The external wireless communication unit may wirelessly transmit external advice information input through the external input device to the terminal-side wireless communication unit, and the external advice information may be displayed on the terminal monitor.

The external apparatus may include a measurement unit that analyzes the ultrasound image to perform measurement on a measurement target in the ultrasound image.

The mobile information terminal may include a measurement unit that analyzes the ultrasound image to perform measurement on a measurement target in the ultrasound image.

The ultrasound system may further include a server that is connected to the mobile information terminal and the external apparatus, and the server may include a measurement unit that analyzes the ultrasound image to perform measurement on a measurement target in the ultrasound image.

Wireless communication of voice data may be performed between the terminal-side wireless communication unit and the external wireless communication unit in two directions.

There is provided a method of controlling a first ultrasound system according to the present invention that is a method of controlling an ultrasound system including an ultrasound probe, a mobile information terminal, and an external apparatus, the method comprising, at the ultrasound probe, transmitting an ultrasonic wave from a transducer array of the ultrasound probe and generating a sound ray signal based on a reception signal acquired by the transducer array, generating an ultrasound image based on the generated sound ray signal, and wirelessly transmitting the ultrasound image, at the mobile information terminal, acquiring a view image obtained by imaging a scanning point of the ultrasound probe in a subject, and wirelessly transmitting the acquired view image, and at the external apparatus, displaying the ultrasound image wirelessly transmitted from the ultrasound probe and the view image wirelessly transmitted from the mobile information terminal on the external monitor, in which, in a case where a probe freeze instruction is input from an external input device of the external apparatus, the probe freeze instruction is transmitted from the external apparatus, and the transmission of the ultrasonic wave from the transducer array of the ultrasound probe is stopped.

There is provided a second ultrasound system according to the present invention that is an ultrasound system comprising an ultrasound probe, a mobile information terminal, and an external apparatus, in which the ultrasound probe includes a transducer array, a transmission and reception circuit that transmits an ultrasonic wave from the transducer array and generates a sound ray signal based on a reception signal acquired by the transducer array, a reception data generation unit that generates reception data before imaging by executing signal processing on the sound ray signal generated by the transmission and reception circuit, and a probe-side wireless communication unit that wirelessly transmits the reception data, the mobile information terminal includes a camera unit that acquires a view image obtained by imaging a scanning point of the ultrasound probe in a subject, and a terminal-side wireless communication unit that wirelessly transmits the view image acquired by the camera unit, the external apparatus includes an external wireless communication unit that is wirelessly connected to at least the terminal-side wireless communication unit, an external monitor, a display controller that displays an ultrasound image generated based on the reception data wirelessly transmitted from the ultrasound probe and the view image wirelessly transmitted from the mobile information terminal on the external monitor, and an external input device, and in a case where a probe freeze instruction is input from the external input device, the probe freeze instruction is transmitted from the external wireless communication unit and the transmission of the ultrasonic wave from the transducer array by the transmission and reception circuit of the ultrasound probe is stopped.

It is preferable that, in a case where the probe freeze instruction is input from the external input device, the probe freeze instruction is transmitted from the external wireless communication unit to the probe-side wireless communication unit through the terminal-side wireless communication unit.

In this case, in a case where the probe freeze instruction is input from the external input device, the acquisition of the view image by the camera unit of the mobile information terminal may be stopped.

In a case where the probe freeze instruction is input from the external input device, the probe freeze instruction may be transmitted from the external wireless communication unit to the probe-side wireless communication unit.

The external wireless communication unit may be wirelessly connected to both the probe-side wireless communication unit and the terminal-side wireless communication unit, and the probe-side wireless communication unit may wirelessly transmit the reception data to both the mobile information terminal and the external apparatus.

The probe-side wireless communication unit may wirelessly transmit the reception data to the mobile information terminal, and the terminal-side wireless communication unit may wirelessly transmit the ultrasound image wirelessly transmitted from the probe-side wireless communication unit and the view image acquired by the camera unit to the external apparatus.

The external apparatus may include an image processing unit that generates the ultrasound image based on the reception data wirelessly transmitted from the probe-side wireless communication unit.

The probe-side wireless communication unit may wirelessly transmit the reception data to the mobile information terminal, the mobile information terminal may include an image processing unit that generates the ultrasound image based on the reception data wirelessly transmitted from the probe-side wireless communication unit, and the terminal-side wireless communication unit may wirelessly transmit the ultrasound image generated by the image processing unit and the view image acquired by the camera unit to the external apparatus.

The external monitor may include a microphone, and the stop of the transmission of the ultrasonic wave from the transducer array may be released by voice input through the microphone.

The external apparatus may include an image synchronization unit that synchronizes the ultrasound image and the view image with each other.

In this case, the external apparatus may include an image memory that stores the ultrasound image and the view image synchronized with each other by the image synchronization unit each time the probe freeze instruction is input from the external input device, and a thumbnail image generation unit that generate a plurality of thumbnail images each consisting of the ultrasound image and the view image stored in the image memory and displays the plurality of generated thumbnail images in a list on the external monitor.

The mobile information terminal may include a terminal monitor, and the ultrasound image and the view image may be displayed on the terminal monitor.

In this case, it is preferable that the mobile information terminal includes a terminal input device, and in a case where the probe freeze instruction is input from the external input device or the terminal input device, guidance on the probe freeze instruction is displayed on the external monitor and the terminal monitor.

The external input device may have a touch sensor disposed on the external monitor in a superimposed manner, the terminal input device may have a touch sensor disposed on the terminal monitor in a superimposed manner, and in a case where the probe freeze instruction is input from the external input device or the terminal input device, as any one of a release button displayed on the external monitor, display for guidance on the probe freeze instruction displayed on the external monitor, a release button displayed on the terminal monitor, or display for guidance on the probe freeze instruction displayed on the terminal monitor may be touched, the stop of the transmission of the ultrasonic wave from the transducer array may be released.

The mobile information terminal may include a microphone, and the stop of the transmission of the ultrasonic wave from the transducer array may be released by voice input through the microphone.

The mobile information terminal may include an image synchronization unit that synchronizes the ultrasound image and the view image with each other.

The external wireless communication unit may wirelessly transmit external advice information input through the external input device to the terminal-side wireless communication unit, and the external advice information may be displayed on the terminal monitor.

The external apparatus may include a measurement unit that analyzes the ultrasound image to perform measurement on a measurement target in the ultrasound image.

The mobile information terminal may include a measurement unit that analyzes the ultrasound image to perform measurement on a measurement target in the ultrasound image.

The ultrasound system may further comprise a server that is connected to the mobile information terminal and the external apparatus, and the server may include a measurement unit that analyzes the ultrasound image to perform measurement on a measurement target in the ultrasound image.

Wireless communication of voice data may be performed between the terminal-side wireless communication unit and the external wireless communication unit in two directions.

There is provided a method of controlling a second ultrasound system according to the present invention that is a method of controlling an ultrasound system including an ultrasound probe, a mobile information terminal, and an external apparatus, the method comprising, at the ultrasound probe, transmitting an ultrasonic wave from a transducer array of the ultrasound probe and generating a sound ray signal based on a reception signal acquired by the transducer array, generating an ultrasound image based on the generated sound ray signal, and wirelessly transmitting the ultrasound image, at the mobile information terminal, acquiring a view image obtained by imaging a scanning point of the ultrasound probe in a subject, and wirelessly transmitting the acquired view image, and at the external apparatus, displaying the ultrasound image wirelessly transmitted from the ultrasound probe and the view image wirelessly transmitted from the mobile information terminal on the external monitor, in which, in a case where a probe freeze instruction is input from an external input device of the external apparatus, the probe freeze instruction is transmitted from the external apparatus, and the transmission of the ultrasonic wave from the transducer array of the ultrasound probe is stopped.

According to the present invention, the external apparatus includes the external wireless communication unit that is wirelessly connected to at least the terminal-side wireless communication unit, the external monitor, the display controller that displays the ultrasound image wirelessly transmitted from the ultrasound probe and the view image wirelessly transmitted from the mobile information terminal on the external monitor, and the external input device, and in a case where the probe freeze instruction is input from the external input device, the probe freeze instruction is transmitted from the external wireless communication unit, and the transmission of the ultrasonic wave from the transducer array by the transmission and reception circuit of the ultrasound probe is stopped. Therefore, even in a case where an ultrasound image is captured at a remote location, an appropriate ultrasound image is obtained, and it is possible to improve accuracy of ultrasound diagnosis.

DESCRIPTION OF THE PREFERRED EMBODIMENTS

Hereinafter, embodiments of the present invention will be described referring to the accompanying drawings.

The description of components described below is provided based on a representative embodiment of the present invention, but the present invention is not limited to such an embodiment.

In the specification, a numerical range represented using "to" means a range including numerical values before and after "to" as a lower limit value and an upper limit value.

In the specification, the terms "same" and "identical" include an error range allowed in the technical field.

Embodiment 1

Figure 1:
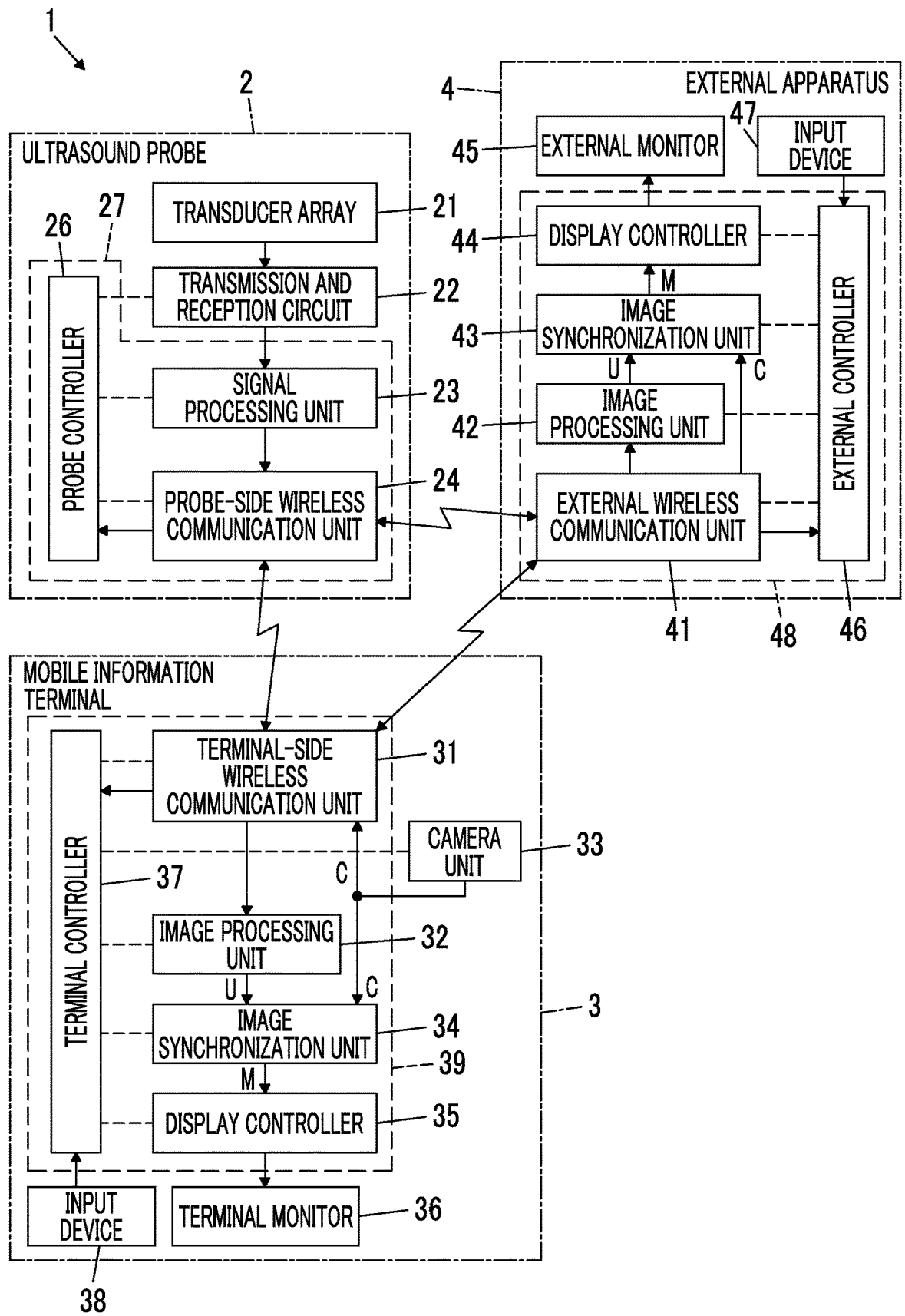
FIG. 1 is a block diagram showing the configuration of an ultrasound system according to Embodiment 1 of the present invention.

FIG. 1 shows the configuration of an ultrasound system 1 according to Embodiment 1 of the present invention. The ultrasound system 1 comprises an ultrasound probe 2, a mobile information terminal 3, and an external apparatus 4. The mobile information terminal 3 and the external apparatus 4 are connected to the ultrasound probe 2 by wireless communication, and the mobile information terminal 3 and the external apparatus 4 are connected to each other by wireless communication.

The ultrasound probe 2 comprises a transducer array 21, and a transmission and reception circuit 22, a signal processing unit 23, and a probe-side wireless communication unit 24 are sequentially connected to the transducer array 21. The probe-side wireless communication unit 24 is connected to the mobile information terminal 3 and the external apparatus 4 by wireless communication. Though not shown, the signal processing unit 23 configures a reception data generation unit.

A probe controller 26 is connected to the transmission and reception circuit 22, the signal processing unit 23, and the probe-side wireless communication unit 24. The signal processing unit 23, the probe-side wireless communication unit 24, and the probe controller 26 configure a probe-side processor 27.

The mobile information terminal 3 comprises a terminal-side wireless communication unit 31 that is connected to the ultrasound probe 2 and the external apparatus 4 by wireless communication, and an image processing unit 32 is connected to the terminal-side wireless communication unit 31. The mobile information terminal 3 comprises a camera unit 33, and the camera unit 33 is connected to the terminal-side wireless communication unit 31. An image synchronization unit 34 is connected to the image processing unit 32 and the camera unit 33.

A display controller 35 and a terminal monitor 36 are sequentially connected to the image synchronization unit 34. A terminal controller 37 is connected to the terminal-side wireless communication unit 31, the image processing unit 32, the camera unit 33, the image synchronization unit 34, and the display controller 35. An input device (terminal input device) 38 is connected to the terminal controller 37. The terminal-side wireless communication unit 31, the image processing unit 32, the image synchronization unit 34, the display controller 35, and the terminal controller 37 configure a terminal-side processor 39.

The external apparatus 4 comprises an external wireless communication unit 41 that is connected to the ultrasound probe 2 and the mobile information terminal 3 by wireless communication, and an image processing unit 42 and an image synchronization unit 43 are connected to the external wireless communication unit 41. The image processing unit 42 is connected to the image synchronization unit 43. A display controller 44 and an external monitor 45 are sequentially connected to the image synchronization unit 43.

An external controller 46 is connected to the external wireless communication unit 41, the image processing unit 42, the image synchronization unit 43, and the display controller 44. An input device (external input device) 47 is connected to the external controller 46. The external wireless communication unit 41, the image processing unit 42, the image synchronization unit 43, the display controller 44, and the external controller 46 configure an external apparatus-side processor 48.

The transducer array 21 of the ultrasound probe 2 has a plurality of transducers arranged in a one-dimensional or two-dimensional manner. Each transducer transmits an ultrasonic wave in response to a drive signal supplied from the transmission and reception circuit 22, receives an ultrasound echo from a subject, and outputs a reception signal based on the ultrasound echo. Each transducer is constituted by forming electrodes at both ends of a piezoelectric body made of, for example, piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
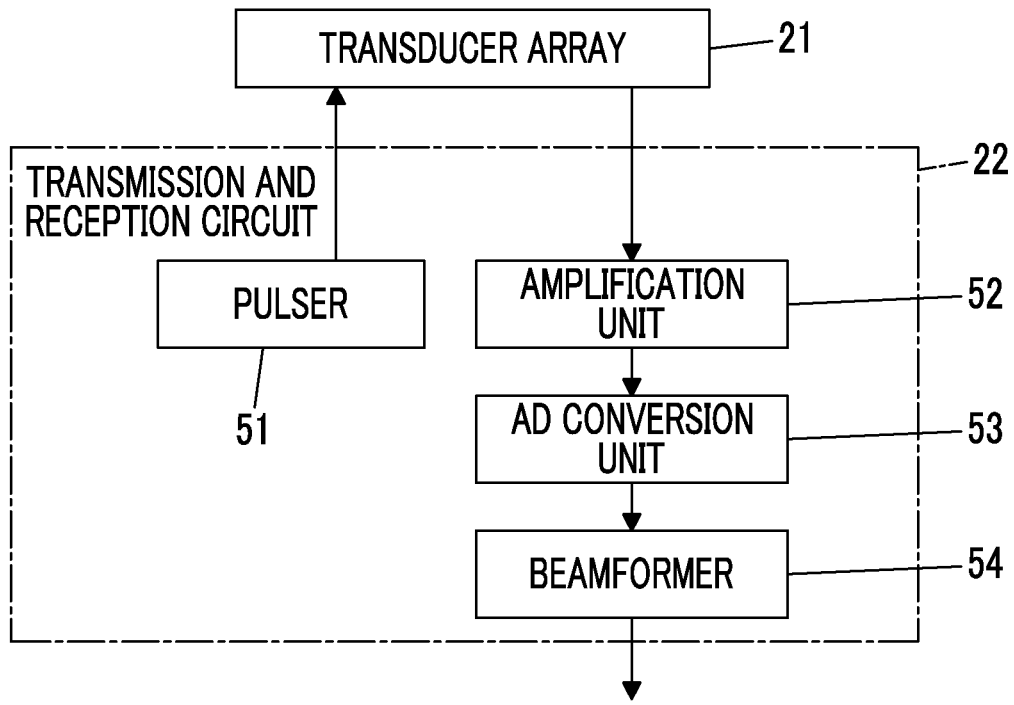
FIG. 2 is a block diagram showing the internal configuration of a transmission and reception circuit in Embodiment 1 of the present invention.

The transmission and reception circuit 22 transmits an ultrasonic wave from the transducer array 21 and generates a sound ray signal based on the reception signal acquired by the transducer array 21 under the control of the probe controller 26. As shown in FIG. 2, the transmission and reception circuit 22 has a pulser 51 that is connected to the transducer array 21, and an amplification unit 52, an analog-digital (AD) conversion unit 53, and a beamformer 54 connected in series from the transducer array 21.

The pulser 51 includes, for example, a plurality of pulse generators, and adjusts a delay amount of each drive signal based on a transmission delay pattern selected in response to a control signal from the probe controller 26 such that the ultrasonic waves transmitted from a plurality of transducers of the transducer array 21 form an ultrasonic beam, and supplies the drive signals to a plurality of transducers. In this way, in a case where a pulsed or continuous-wave voltage is applied to the electrodes of each of a plurality of transducers of the transducer array 21, the piezoelectric body expands and contracts to generate a pulsed or continuous-wave ultrasonic wave from each of the transducers. An ultrasonic beam is formed from a combined wave of the ultrasonic waves.

The transmitted ultrasonic beam is reflected by, for example, a target, such as a part of the subject, and propagates toward the transducer array 21 of the ultrasound probe 2. The ultrasound echo propagating toward the transducer array 21 is received by each transducer configuring the transducer array 21, and each transducer expands and contracts with reception of the propagating ultrasound echo to generate a reception signal as an electrical signal, and outputs the reception signal to the amplification unit 52.

The amplification unit 52 amplifies the signal input from each transducer configuring the transducer array 21 and transmits the amplified signal to the AD conversion unit 53. The AD conversion unit 53 converts the signal transmitted from the amplification unit 52 into digital reception data and transmits the reception data to the beamformer 54. The beamformer 54 executes so-called reception focus processing by giving a delay to each piece of reception data converted by the AD conversion unit 53 conforming to a sound speed or a distribution of a sound speed set based on a reception delay pattern selected in response to a control signal from the probe controller 26 and performing addition. With the reception focus processing, each piece of reception data converted by the AD conversion unit 53 is phased and added, and a sound ray signal in which the focus of the ultrasound echo is narrowed is acquired.

The signal processing unit 23 generates reception data before imaging by executing signal processing based on the sound ray signal generated by the beamformer 54 of the transmission and reception circuit 22. More specifically, the signal processing unit 23 performs correction of attenuation on the sound ray signal generated by the beamformer 54 of the transmission and reception circuit 22 due to a propagation distance depending on a depth of a position where the ultrasonic wave is reflected, and then, executes envelope detection processing to generate a signal representing tomographic image information regarding a tissue in the subject as reception data before imaging.

The probe-side wireless communication unit 24 includes an antenna that performs transmission and reception of radio waves, and modulates a carrier based on the reception data before imaging generated by the signal processing unit 23 to generate a transmission signal representing the reception data before imaging. The probe-side wireless communication unit 24 supplies the transmission signal generated in this manner to the antenna and transmits the radio waves from the antenna, thereby sequentially wirelessly transmitting the reception data before imaging to the terminal-side wireless communication unit 31 of the mobile information terminal 3 and the external wireless communication unit 41 of the external apparatus 4. As a modulation system of the carrier, for example, amplitude shift keying (ASK), phase shift keying (PSK), quadrature phase shift keying (QPSK), 16 quadrature amplitude modulation (16QAM), or the like is used.

The wireless communication among the probe-side wireless communication unit 24 of the ultrasound probe 2, the terminal-side wireless communication unit 31 of the mobile information terminal 3, and the external wireless communication unit 41 of the external apparatus 4 can be performed conforming to a communication standard regarding mobile communication, such as a 5th Generation mobile communication system (5G) or a 4th Generation mobile communication system (4G), or a communication standard regarding short-distance wireless communication, such as WiFi (Registered Trademark), Bluetooth (Registered Trademark), or an ultra wide band wireless system (UWB).

It is assumed that the ultrasound probe 2 and the mobile information terminal 3 are positioned close to each other, and thus, as the wireless communication between the ultrasound probe 2 and the mobile information terminal 3, any wireless communication system of mobile communication or short-distance wireless communication may be employed.

It is assumed that the external apparatus 4 is positioned at a remote location with respect to the ultrasound probe 2 and the mobile information terminal 3, and thus, it is preferable that, as the wireless communication between the external apparatus 4 and the ultrasound probe 2 and the wireless communication between the external apparatus 4 and the mobile information terminal 3, mobile communication is performed. In particular, from a viewpoint of reducing a time lag in transmission of data between the external apparatus 4, and the ultrasound probe 2 and the mobile information terminal 3, it is preferable that, as the wireless communication between the external apparatus 4 and the ultrasound probe 2 and the wireless communication between the external apparatus 4 and the mobile information terminal 3, mobile communication conforming to 5G is performed.

The probe controller 26 performs control of each unit of the ultrasound probe 2 based on a control program and the like stored in advance.

Though not shown, a probe-side storage unit is connected to the probe controller 26. The probe-side storage unit stores the control program and the like of the ultrasound probe 2. As the probe-side storage unit, for example, a flash memory, a random access memory (RAM), a secure digital card (SD), or a solid state drive (SSD) can be used.

Though not shown, a battery is incorporated in the ultrasound probe 2, and power is supplied from the battery to each circuit of the ultrasound probe 2.

Although the probe-side processor 27 having the signal processing unit 23, the probe-side wireless communication unit 24, and the probe controller 26 is configured with a central processing unit (CPU) and a control program causing the CPU to execute various kinds of processing, the probe-side processor 27 may be configured using a field programmable gate array (FPGA), a digital signal processor (DSP), an application specific integrated circuit (ASIC), a graphics processing unit (GPU), or other integrated circuits (ICs) or may be configured by combining such ICs.

The signal processing unit 23, the probe-side wireless communication unit 24, and the probe controller 26 of the probe-side processor 27 may be configured to be partially or wholly integrated into one CPU or the like.

The terminal-side wireless communication unit 31 of the mobile information terminal 3 includes an antenna that performs transmission and reception of radio waves, and receives the transmission signal representing the reception data before imaging transmitted from the probe-side wireless communication unit 24 of the ultrasound probe 2, through the antenna and outputs the reception data before imaging by demodulating the received transmission signal under the control of the terminal controller 37. The terminal-side wireless communication unit 31 sends the reception data before imaging to the image processing unit 32.

The image processing unit 32 raster-converts the reception data before imaging sent from the terminal-side wireless communication unit 31 into an image signal conforming to a normal television signal scanning system and executes various kinds of necessary image processing, such as brightness correction, gradation correction, sharpness correction, an image size correction, refresh rate correction, scanning frequency correction, and color correction, conforming to a display format for the terminal monitor 36 on the converted image signal, thereby generating a brightness mode (B mode) image signal. The B mode image signal generated in this manner is simply referred to as an ultrasound image U. The image processing unit 32 sends the generated ultrasound image U to the image synchronization unit 34.

The camera unit 33 acquires a view image C obtained by imaging a scanning point of the ultrasound probe 2 in the subject. Though not shown, the camera unit 33 incorporates an imaging lens, an image sensor that images the scanning point of the ultrasound probe 2 through the imaging lens to acquire a view image signal as an analog signal, an analog signal processing circuit that amplifies the view image signal acquired by the image sensor and converts the view image signal into a digital signal, and a digital signal processing circuit that performs various kinds of correction, such as a gain, on the converted digital signal to generate the view image C. The analog signal processing circuit and the digital signal processing circuit may be incorporated in the terminal-side processor 39. The camera unit 33 sends the generated view image C to the terminal-side wireless communication unit 31 and the image synchronization unit 34. The terminal-side wireless communication unit 31 wirelessly transmits the view image C sent to the terminal-side wireless communication unit 31 to the external apparatus 4.

The image synchronization unit 34 synchronizes the ultrasound image U generated by the image processing unit 32 and the view image C generated by the camera unit 33 with each other to generate a composite image M based on the ultrasound image U and the view image C synchronized with each other. Here, synchronizing the ultrasound image U and the view image C with each other refers to associating the ultrasound image U and the view image C captured at the same timing with each other. For example, in a case where a time stamp representing a time at which the ultrasound image U is generated is given to the ultrasound image U by the image processing unit 32, and a time stamp representing a time at which the view image C is generated is given to the view image C by the camera unit 33, the image synchronization unit 34 can synchronize the ultrasound image U and the view image C captured at the same timing with each other by regarding the time stamp of the ultrasound image U as representing the time at which the ultrasound image U is captured, regarding the time stamp of the view image C as representing a time at which the view image C is captured, and referring to the time stamps of the ultrasound image U and the view image C.

In associating the ultrasound image U and the view image C with each other, for example, the image synchronization unit 34 can refer to the time stamp of the ultrasound image U and the time stamp of the view image C, and in a case where a difference between the time at which the ultrasound image U is captured and the time at which the view image C is captured is within a given range, for example, within 0.1 seconds, can regard the ultrasound image U and the view image C as being captured at the same timing to perform association. Alternatively, for example, the image synchronization unit 34 may refer to the time stamp of the ultrasound image U and the time stamp of the view image C, may select the view image C captured at a time closest to the time at which the ultrasound image U to be associated is captured, and may associate the selected view image C and the ultrasound image U with each other. For example, the image synchronization unit 34 may select the ultrasound image U captured at a time closest to the time at which the view image C to be associated is captured, and may associate the selected ultrasound image U and the view image C with each other.

The image synchronization unit 34 sends the ultrasound image U and the view image C synchronized in this manner to the display controller 35.

Figure 3:
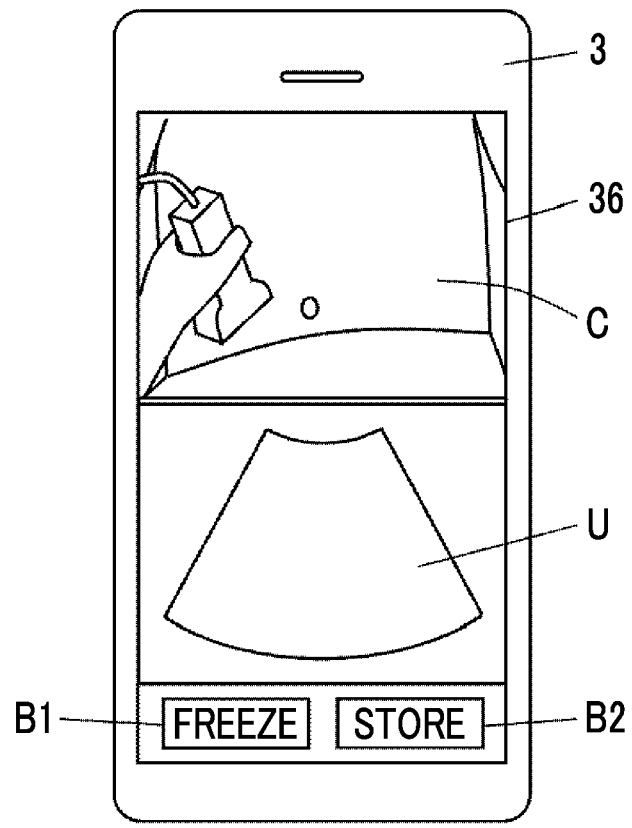
FIG. 3 is a diagram schematically showing an example of a mobile information terminal in Embodiment 1 of the present invention.

The display controller 35 executes predetermined processing on the composite image M sent from the image synchronization unit 34 and displays the ultrasound image U and the view image C synchronized with each other together on the terminal monitor 36 of the mobile information terminal 3 as shown in FIG. 3 under the control of the terminal controller 37. In an example shown in FIG. 3, in addition to the ultrasound image U and the view image C, a freeze button B1 for freezing the ultrasound image U and a store button B2 for storing the ultrasound image U and the view image C are displayed. Here, freezing the ultrasound image U refers to temporarily stopping generation of an ultrasound image U by stopping the transmission of the ultrasonic wave from the transducer array 21. In this way, the display controller 35 can display a so-called user interface, such as the freeze button B1 and the store button B2, on the terminal monitor 36 under the control of the terminal controller 37.

The terminal monitor 36 displays the ultrasound image U, the view image C, and the like under the control of the display controller 35, and includes, for example, a display device, such as a liquid crystal display (LCD) or an organic electroluminescence display (organic EL display).

The input device 38 of the mobile information terminal 3 is provided for the operator to perform an input operation, and includes a touch sensor disposed on the terminal monitor 36 in a superimposed manner. For example, probe control information for controlling the ultrasound probe 2 can be input from the operator through the input device 38. The probe control information input in this manner is sent to the terminal-side wireless communication unit 31 by way of the terminal controller 37 and is wirelessly transmitted from the terminal-side wireless communication unit 31 to the ultrasound probe 2.

The terminal controller 37 performs control of each unit of the mobile information terminal 3 based on a control program and the like stored in advance.

Though not shown, a terminal-side storage unit is connected to the terminal controller 37. The terminal-side storage unit stores the control program and the like of the mobile information terminal 3. As the terminal-side storage unit, for example, a flash memory, a RAM, an SD card, or an SSD can be used.

Though not shown, a battery is incorporated in the mobile information terminal 3, and power is supplied from the battery to each circuit of the mobile information terminal 3.

Although the terminal-side processor 39 having the terminal-side wireless communication unit 31, the image processing unit 32, the image synchronization unit 34, the display controller 35, and the terminal controller 37 is configured with a CPU and a control program causing the CPU to execute various kinds of processing, the terminal-side processor 39 may be configured using an FPGA, a DSP, an ASIC, a GPU, or other ICs or may be configured by combining such ICs.

The terminal-side wireless communication unit 31, the image processing unit 32, the image synchronization unit 34, the display controller 35, and the terminal controller 37 of the terminal-side processor 39 may be configured to be partially or wholly integrated into one CPU or the like.

The external wireless communication unit 41 of the external apparatus 4 includes an antenna that performs transmission and reception of radio waves, and receives the transmission signal representing the reception data before imaging transmitted from the probe-side wireless communication unit 24 of the ultrasound probe 2 and the transmission signal representing the view image C transmitted from the terminal-side wireless communication unit 31 of the mobile information terminal 3, through the antenna and outputs the reception data before imaging and the view image C by demodulating the received transmission signals under the control of the external controller 46. The external wireless communication unit 41 sends the reception data before imaging to the image processing unit 42 and sends the view image C to the image synchronization unit 43.

The image processing unit 42 raster-converts the reception data before imaging sent from the external wireless communication unit 41 into an image signal conforming to a normal television signal scanning system and executes various kinds of necessary image processing, such as brightness correction, gradation correction, sharpness correction, image size correction, refresh rate correction, scanning frequency correction, and color correction, conforming to a display format for the external monitor 45 on the converted image signal, thereby generating an ultrasound image U. The image processing unit 42 sends the generated ultrasound image U to the image synchronization unit 43.

The image synchronization unit 43 of the external apparatus 4 synchronizes the ultrasound image U sent from the image processing unit 42 and the view image C sent from the external wireless communication unit 41 with each other to generate a composite image M based on the ultrasound image U and the view image C synchronized with each other. For example, in a case where a time stamp representing at time at which the ultrasound image U is generated is given to the ultrasound image U by the image processing unit 42 of the external apparatus 4, and a time stamp representing a time at which the view image C is generated is given to the view image C by the camera unit 33 of the mobile information terminal 3, the image synchronization unit 43 can synchronize the ultrasound image U and the view image C captured at the same timing with each other by regarding the time stamp of the ultrasound image U as representing a time at which the ultrasound image U is captured, regarding the time stamp of the view image C as representing a time at which the view image C is captured, and referring to the time stamps of the ultrasound image U and the view image C.

Figure 4:
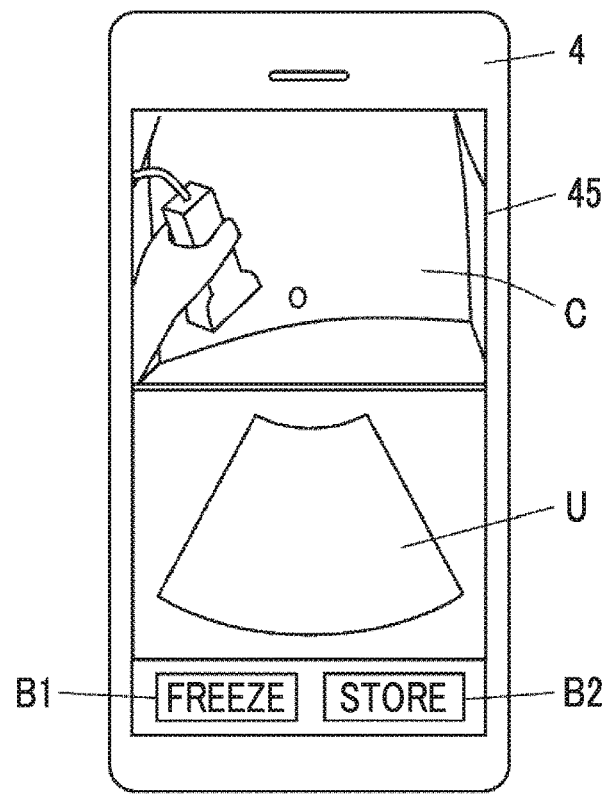
FIG. 4 is a diagram schematically showing an example of an external apparatus in Embodiment 1 of the present invention.

The display controller 44 executes predetermined processing on the composite image M sent from the image synchronization unit 43 and displays the ultrasound image U and the view image C synchronized with each other together on the external monitor 45 of the external apparatus 4 as shown in FIG. 4 under the control of the external controller 46. In an example shown in FIG. 4, in addition to the ultrasound image U and the view image C, a freeze button B1 and a store button B2 are displayed. In this way, the display controller 44 can display a so-called user interface, such as the freeze button B1 and the store button B2, on the external monitor 45.

The external monitor 45 displays the ultrasound image U, the view image C, and the like under the control of the display controller 44, and includes, for example, a display device, such as an LCD or an organic EL display.

The input device 47 of the external apparatus 4 is provided for the operator to perform an input operation, and includes a touch sensor disposed on the external monitor 45 in a superimposed manner.

The external controller 46 performs control of each unit of the external apparatus 4 based on a control program and the like stored in advance.

Though not shown, an external apparatus-side storage unit is connected to the external apparatus 4. The external apparatus-side storage unit stores the control program and the like of the external apparatus 4. As the external apparatus-side storage unit, for example, a flash memory, a RAM, an SD card, or an SSD can be used.

Though not shown, a battery is incorporated in the external apparatus 4, and power is supplied from the battery to each circuit of the external apparatus 4.

Although the external apparatus-side processor 48 having the external wireless communication unit 41, the image processing unit 42, the image synchronization unit 43, the display controller 44, and the external controller 46 is configured with a CPU and a control program causing the CPU to execute various kinds of processing, the external apparatus-side processor 48 may be constituted using an FPGA, a DSP, an ASIC, a GPU, or other ICs or may be constituted by combining such ICs.

The external wireless communication unit 41, the image processing unit 42, the image synchronization unit 43, the display controller 44, and the external controller 46 of the external apparatus-side processor 48 may be configured to be partially or wholly integrated into one CPU or the like.

Next, the operation of the ultrasound system 1 according to Embodiment 1 of the present invention will be described.

First, the ultrasound probe 2 is brought into contact with a body surface of the subject by the operator, and ultrasonic beams are transmitted from a plurality of transducers of the transducer array 21 into the subject in response to the drive signals from the puller 51 of the transmission and reception circuit 22 under the control of the probe controller 26. An ultrasound echo based on the transmitted ultrasonic beam is received by each transducer, the reception signal as an analog signal is output to the amplification unit 52 and amplified, and is AD-converted by the AD conversion unit 53, and reception data is acquired. The beamformer 54 executes the reception focus processing on the reception data to generate a sound ray signal.

The signal processing unit 23 converts the generated sound ray signal into reception data before imaging that is a signal representing tomographic image information regarding a tissue in the subject. In this case, the signal processing unit 23 performs correction of attenuation on the sound ray signal due to a propagation distance depending on a depth of a position where the ultrasonic wave is reflected, and then, executes envelope detection processing.

The probe-side wireless communication unit 24 wirelessly transmits the generated sound ray signal to the mobile information terminal 3 and the external apparatus 4.

The terminal-side wireless communication unit 31 of the mobile information terminal 3 receives the reception data before imaging wirelessly transmitted from the ultrasound probe 2 and sends the received reception data before imaging to the image processing unit 32. The image processing unit 32 raster-converts the reception data before imaging sent from the terminal-side wireless communication unit 31 into an image signal conforming to a normal television signal scanning system and executes various kinds of necessary image processing, such as brightness correction, gradation correction, sharpness correction, image size correction, refresh rate correction, scanning frequency correction, and color correction, conforming to a display format for the terminal monitor 36 on the converted image signal, thereby generating the ultrasound image U. The ultrasound image U generated in this manner is sent to the image synchronization unit 34.

The camera unit 33 of the mobile information terminal 3 acquires the view image C obtained by imaging the scanning point of the ultrasound probe 2 in the subject under the control of the terminal controller 37. Though not shown, in this case, for example, the operator can input control information for imaging the view image C through the input device 38 of the mobile information terminal 3 while directing the imaging lens of the camera unit 33 toward the scanning point of the ultrasound probe 2 in the subject. In this case, for example, the control information input from the operator is input to the terminal controller 37, and the terminal controller 37 can control the camera unit 33 to capture the view image C conforming to the control information. The view image C acquired in this manner is sent to the terminal-side wireless communication unit 31 and the image synchronization unit 34.

In a case where the ultrasound image U is received from the image processing unit 32 and the view image C is received from the camera unit 33, the image synchronization unit 34 synchronizes the received ultrasound image U and view image C with each other to generate the composite image M in which the ultrasound image U and the view image C synchronized with each other are put together into one image. For example, in a case where the time stamp representing the time at which the ultrasound image U is generated is given to the ultrasound image U by the image processing unit 32, and the time stamp representing the time at which the view image C is generated is given to the view image C by the camera unit 33, the image synchronization unit 34 can associate the ultrasound image U and the view image C captured at the same timing with each other by regarding the time stamp of the ultrasound image U as representing the time at which the ultrasound image U is captured, regarding the time stamp of the view image C as representing the time at which the view image C is captured, and referring to the time stamps of the ultrasound image U and the view image C.

The ultrasound image U and the view image C synchronized with each other by the image synchronization unit 34 are sent as the composite image M to the display controller 35. The display controller 35 executes predetermined processing on the composite image M, then, sends the composite image M to the terminal monitor 36, and displays the ultrasound image U and the view image C together on the terminal monitor 36 as shown in FIG. 3. In the example shown in FIG. 3, the view image C and the ultrasound image U are displayed on the upper and lower sides of the terminal monitor 36, respectively. In this example, a state in which the ultrasound probe 2 is in contact with an abdomen of the subject is rendered in the view image C, and an internal tissue of the abdomen of the subject is rendered in the ultrasound image U. For this reason, the operator can confirm the view image C representing the scanning point of the ultrasound probe 2 in the subject and the ultrasound image U corresponding to the view image C simultaneously by confirming the terminal monitor 36 of the mobile information terminal 3, and can easily correspond and recognize the scanning point of the ultrasound probe 2 in the subject and the tissue in the subject to be observed at the scanning point.

The view image C acquired by the camera unit 33 is wirelessly transmitted from the terminal-side wireless communication unit 31 to the external apparatus 4.

The external wireless communication unit 41 of the external apparatus 4 receives the reception data before imaging wirelessly transmitted from the ultrasound probe 2 and the view image C wirelessly transmitted from the mobile information terminal 3, sends the received reception data before imaging to the image processing unit 42, and sends the received view image C to the image synchronization unit 43.

The image processing unit 42 raster-converts the reception data before imaging sent from the external wireless communication unit 41 into an image signal conforming to a normal television signal scanning system and executes various kinds of necessary image processing, such as brightness correction, gradation correction, sharpness correction, image size correction, refresh rate correction, scanning frequency correction, and color correction, conforming to a display format for the external monitor 45 on the converted image signal, thereby generating an ultrasound image U. The image processing unit 42 sends the generated ultrasound image U to the image synchronization unit 43.

The image synchronization unit 43 synchronizes the ultrasound image U sent from the image processing unit 42 and the view image C sent from the external wireless communication unit 41 with each other to generate the composite image M in which the ultrasound image U and the view image C synchronized with each other are put together into one image. For example, in a case where the time stamp representing the time at which the ultrasound image U is generated is given to the ultrasound image U by the image processing unit 42 of the external apparatus 4, and the time stamp representing the time at which the view image C is generated is given to the view image C by the camera unit 33 of the mobile information terminal 3, the image synchronization unit 43 can synchronize the ultrasound image U and the view image C captured at the same timing with each other by regarding the time stamp of the ultrasound image U as representing the time at which the ultrasound image U is captured, regarding the time stamp of the view image C as representing the time at which the view image C is captured, and referring to the time stamps of the ultrasound image U and the view image C. In this case, the time in the mobile information terminal 3 and the time in the external apparatus 4 can be shared by each other.

Although the time in the mobile information terminal 3 and the time in the external apparatus 4 can be shared by each other, specifically, for example, the time can be shared with the mobile information terminal 3 or the external apparatus 4 as a reference. For example, in a case where any one of the mobile information terminal 3 or the external apparatus 4 is connected to the Internet, a time of an internal timepiece may be set using a communication protocol, such as Network Time Protocol (NTP) or Network Identity and Time Zone (NITZ).

The ultrasound image U and the view image C synchronized with each other by the image synchronization unit 43 are sent as the composite image M to the display controller 44. The display controller 44 executes predetermined processing on the composite image M, then, sends the composite image M to the external monitor 45, and displays the ultrasound image U and the view image C together on the external monitor 45 as shown in FIG. 4. In the example of FIG. 4, the external apparatus 4 is shown as a mobile terminal similarly to the mobile information terminal 3, and the view image C and the ultrasound image U are displayed on the upper and lower sides of the terminal monitor 36 of the external apparatus 4. In this example, like the ultrasound image U and the view image C that are displayed on the terminal monitor 36 of the mobile information terminal 3, a state in which the ultrasound probe 2 is in contact with the abdomen of the subject is rendered in the view image C, and the internal tissue of the abdomen of the subject is rendered in the ultrasound image U.

Here, although the view image C and the ultrasound image U synchronized with each other are displayed on the terminal monitor 36 of the mobile information terminal 3 and the external monitor 45 of the external apparatus 4, the same view image C and ultrasound image U are displayed on the terminal monitor 36 and the external monitor 45 substantially simultaneously. For this reason, for example, even in a case where the external apparatus 4 is positioned at a remote location with respect to the mobile information terminal 3, the observer who observes the external monitor 45 can observe the view image C and the ultrasound image U captured in a site of inspection where the subject and the operator are positioned, substantially in real time.

In a case where a probe freeze instruction representing the guidance on freezing the ultrasound image U is input from the operator of the ultrasound probe 2 and the mobile information terminal 3 through the input device 38 of the mobile information terminal 3, the input probe freeze instruction is input to the terminal controller 37. The terminal controller 37 performs control such that camera unit 33 stops the imaging of the view image C, with the input of the probe freeze instruction as a trigger.

The terminal-side wireless communication unit 31 wirelessly transmits the probe freeze instruction sent from the terminal controller 37 to the probe-side wireless communication unit 24 of the ultrasound probe 2. The probe-side wireless communication unit 24 receives the probe freeze instruction wirelessly transmitted from the probe-side wireless communication unit 24 and inputs the received probe freeze instruction to the probe controller 26. The probe controller 26 performs control such that the transmission and reception circuit 22 stops the transmission of the ultrasonic wave from the transducer array 21, in response to the probe freeze instruction, and the transmission of the ultrasonic wave from the transducer array 21 is stopped.

In this manner, as the probe freeze instruction is input through the input device 38 of the mobile information terminal 3, the transmission of the ultrasonic wave from the transducer array 21 of the ultrasound probe 2 and the imaging of the view image C by the camera unit 33 of the mobile information terminal 3 are stopped. With this, in the terminal monitor 36 of the mobile information terminal 3, the display of the ultrasound image U and the view image C is temporarily stopped, and the ultrasound image U and the view image C immediately before the transmission of the ultrasonic wave from the transducer array 21 and the imaging of the view image C by the camera unit 33 are stopped are displayed. Even in the external monitor 45 of the external apparatus 4, similarly to the terminal monitor 36 of the mobile information terminal 3, the display of the ultrasound image U and the view image C is temporarily stopped, and the ultrasound image U and the view image C immediately before the transmission of the ultrasonic wave from the transducer array 21 and the imaging of the view image C by the camera unit 33 are stopped are displayed.

In a case where a probe freeze instruction representing the guidance on freezing the ultrasound image U is input from the observer who the ultrasound image U and the view image C displayed on the external monitor 45, through the input device 47 of the external apparatus 4, the input probe freeze instruction is sent to the external wireless communication unit 41 through the external controller 46. The external wireless communication unit 41 wirelessly transmits the probe freeze instruction to the terminal-side wireless communication unit 31 of the mobile information terminal 3. The terminal-side wireless communication unit 31 wirelessly transmits the probe freeze instruction wirelessly transmitted from the external wireless communication unit 41 of the external apparatus 4 to the probe-side wireless communication unit 24 of the ultrasound probe 2 and inputs the probe freeze instruction to the terminal controller 37.

The probe-side wireless communication unit 24 of the ultrasound probe 2 receives the probe freeze instruction wirelessly transmitted from the terminal-side wireless communication unit 31 of the mobile information terminal 3 and inputs the received probe freeze instruction to the probe controller 26. The probe controller 26 performs control such that the transmission and reception circuit 22 stops the transmission of the ultrasonic wave from the transducer array 21, in response to the probe freeze instruction.

The terminal controller 37 performs control such that the camera unit 33 stops the imaging of the view image C, with the input of the probe freeze instruction as a trigger.

In this manner, as the probe freeze instruction is input through the input device 47 of the external apparatus 4, the transmission of the ultrasonic wave from the transducer array 21 of the ultrasound probe 2 and the imaging of the view image C by the camera unit 33 of the mobile information terminal 3 are stopped. With this, in the terminal monitor 36 of the mobile information terminal 3, the display of the ultrasound image U and the view image C is temporarily stopped, and the ultrasound image U and the view image C immediately before the transmission of the ultrasonic wave from the transducer array 21 and the imaging of the view image C by the camera unit 33 are stopped are displayed. Even in the external monitor 45 of the external apparatus 4, similarly to the terminal monitor 36 of the mobile information terminal 3, the display of the ultrasound image U and the view image C is temporarily stopped, and the ultrasound image U and the view image C immediately before the transmission of the ultrasonic wave from the transducer array 21 and the imaging of the view image C by the camera unit 33 are stopped are displayed.

Incidentally, in general, it is known that a given level or higher of skill is needed to accurately recognize the part in the subject rendered in the ultrasound image by confirming the ultrasound image. Furthermore, it is known that the image quality of the ultrasound image generated in the ultrasound diagnostic apparatus significantly depends on the skill involving the hands of the operator.

For example, in a case where an ultrasound image is captured at a remote location other than a hospital, such as home care, the operator who operates the ultrasound probe to capture the ultrasound image may be different from the observer who observes the captured ultrasound image to perform diagnosis. In this case, the operator normally needs to operate the ultrasound probe to capture an ultrasound image of an intended part in a subject while confirming the obtained ultrasound image personally. However, in particular, in a case where the level of skill of the operator is low, the operator may hardly determine whether or not the intended part of the subject is accurately observed. The operator having a low level of skill may not operate the ultrasound probe using appropriate skill involving the hands, and an ultrasound image with low image quality is obtained.

The observer positioned at a remote location with respect to the subject and the operator confirms the ultrasound image captured by the operator of the ultrasound diagnostic apparatus to perform diagnosis; however, since the observer cannot recognize a state in which the operator captures the ultrasound image, in particular, in a case where the ultrasound image is captured by the operator having a low level of skill, the observer may hardly accurately recognize whether or not the captured ultrasound image is captured by appropriate skill involving the hands.

With the ultrasound system 1 according to Embodiment 1 of the present invention, since the same view image C and ultrasound image U are displayed on the terminal monitor 36 and the external monitor 45 substantially simultaneously, for example, even in a case where the external apparatus 4 is positioned at a remote location with respect to the mobile information terminal 3, the observer who observes the external monitor 45 can observe the view image C and the ultrasound image U captured in a site of inspection where the subject and the operator are positioned, substantially in real time. With this, for example, since the observer having a high level of skill can give advice to the operator in real time, even in a case where the level of skill of the operator positioned at a remote location with respect to the observer is low, an appropriate ultrasound image U is obtained, and it is possible to improve accuracy of ultrasound diagnosis.

With the ultrasound system 1 according to Embodiment 1 of the present invention, for example, the observer who is positioned at a remote location with respect to the operator and has a low level of skill can also be made to confirm the view image C representing a state in which the operator having a high level of skill operates the ultrasound probe 2 and the appropriate ultrasound image U corresponding to the view image C. In this way, the ultrasound system 1 according to Embodiment 1 of the present invention is considerably useful even from a viewpoint of training.

In the ultrasound system 1 according to Embodiment 1 of the present invention, as the observer who observes the ultrasound image U and the view image C displayed on the external monitor 45 inputs the probe freeze instruction through the input device 47 of the external apparatus 4, the transmission of the ultrasonic wave from the transducer array 21 of the ultrasound probe 2 is stopped and the imaging of the view image C by the camera unit 33 of the mobile information terminal 3 is stopped, such that the display of the ultrasound image U and the view image C is stopped in the terminal monitor 36 of the mobile information terminal 3 and the external monitor 45 of the external apparatus 4 simultaneously. For this reason, for example, even in a case where the level of skill of the operator of the ultrasound probe 2 and the mobile information terminal 3 is low and hardly determines whether or not an appropriate ultrasound image U is obtained, the observer having a high level of skill inputs the probe freeze instruction through the input device 47 of the external apparatus 4, whereby the display of the ultrasound image U is temporarily stopped at an appropriate timing in the terminal monitor 36 and the external monitor 45. Accordingly, it is possible to obtain an appropriate ultrasound image U. With this, it is possible to improve accuracy of ultrasound diagnosis.

Although an example where the probe freeze instruction input from the observer who observes the ultrasound image U and the view image C displayed on the external monitor 45, through the input device 47 of the external apparatus 4 is wirelessly transmitted from the external wireless communication unit 41 to the probe-side wireless communication unit 24 of the ultrasound probe 2 through the terminal-side wireless communication unit 31 of the mobile information terminal 3 has been described, a method of wirelessly transmitting the probe freeze instruction is not limited thereto.

For example, the external wireless communication unit 41 can wirelessly transmit the probe freeze instruction to each of both the probe-side wireless communication unit 24 of the ultrasound probe 2 and the terminal-side wireless communication unit 31 of the mobile information terminal 3. In this case, the probe freeze instruction received by the probe-side wireless communication unit 24 of the ultrasound probe 2 is input to the probe controller 26, and the probe controller 26 performs control such that the transmission and reception circuit 22 stops the transmission of the ultrasonic wave from the transducer array 21, based on the input probe freeze instruction. The probe freeze instruction received by the terminal-side wireless communication unit 31 of the mobile information terminal 3 is input to the terminal controller 37. The terminal controller 37 performs control such that the display controller 35 temporarily stops the display of the ultrasound image U and the view image C in the terminal monitor 36 and the camera unit 33 stops the imaging of the view image C, with the input of the probe freeze instruction as a trigger. With this, the transmission of the ultrasonic wave from the transducer array 21 and the imaging of the view image C by the camera unit 33 are stopped, and the display of the ultrasound image U and the view image C is temporarily stopped in the terminal monitor 36 of the mobile information terminal 3 and the external monitor 45 of the external apparatus 4 simultaneously.

For example, the external wireless communication unit 41 can wirelessly transmit the probe freeze instruction only to the probe-side wireless communication unit 24 of the ultrasound probe 2. In this case, the probe freeze instruction received by the probe-side wireless communication unit 24 is input to the probe controller 26 and is wirelessly transmitted to the terminal-side wireless communication unit 31 of the mobile information terminal 3. The probe controller 26 performs control such that the transmission and reception circuit 22 stops the transmission of the ultrasonic wave from the transducer array 21, in response to the probe freeze instruction. The terminal-side wireless communication unit 31 of the mobile information terminal 3 receives the probe freeze instruction wirelessly transmitted from the probe-side wireless communication unit 24 of the ultrasound probe 2 and inputs the received probe freeze instruction to the terminal controller 37. The terminal controller 37 performs control such that the display controller 35 temporarily stops the display of the ultrasound image U and the view image C in the terminal monitor 36, with the input of the probe freeze instruction as a trigger. The terminal controller 37 performs control such that the camera unit 33 stops the imaging of the view image C, with the input of the probe freeze instruction as a trigger.

Although an example where the time stamp is given to the generated ultrasound image U in each of the image processing unit 32 of the mobile information terminal 3 and the image processing unit 42 of the external apparatus 4 has been described, instead of the image processing unit 32 of the mobile information terminal 3 and the image processing unit 42 of the external apparatus 4 giving the time stamp to the ultrasound image U, the signal processing unit 23 of the ultrasound probe 2 may give a time stamp to the signal subjected to the envelope detection processing. In this case, for example, the time in the ultrasound probe 2 and the time in the mobile information terminal 3 are shared by each other, whereby it is possible to synchronize the ultrasound image U generated by the image processing unit 32 of the mobile information terminal 3 and the view image C generated by the camera unit 33 with each other based on the signal given the time stamp, and to synchronize the ultrasound image U generated by the image processing unit 42 of the external apparatus 4 and the view image C generated by the camera unit 33 with each other.

Here, the time in the ultrasound probe 2 and the time in the mobile information terminal 3 can be shared, for example, with the ultrasound probe 2 or the mobile information terminal 3 as a reference. For example, in a case where any one of the ultrasound probe 2 or the mobile information terminal 3 is connected to the Internet, the time of the internal timepiece may be set using a communication protocol, such as NTP or NITZ.

A method of synchronizing the ultrasound image U and the view image C with each other is not limited to the method using the time stamp described above. For example, as disclosed in JP2011-183056A, an imaging timing of the ultrasound image U by the ultrasound probe 2 and an imaging timing of the view image C by the camera unit 33 of the mobile information terminal 3 are synchronized with each other, and a time difference between the time at which the ultrasound image U is captured and the time at which the view image C is captured is within a given range, for example, within 0.1 seconds, the image synchronization unit 34 of the mobile information terminal 3 and the image synchronization unit 43 of the external apparatus 4 can regard that the ultrasound image U and the view image C are captured at the same timing, and can synchronize the ultrasound image U and the view image C with each other.

Although the image synchronization unit 34 of the mobile information terminal 3 generates the composite image M in which the ultrasound image U and the view image C synchronized with each other are put together into one image, and sends the generated composite image M to the display controller 35, instead of generating the composite image M, each of the ultrasound image U and the view image C synchronized with each other may be sent to the display controller 35. In this case, the display controller 35 executes predetermined processing on each of the ultrasound image U and the view image C sent from the image synchronization unit 34 and displays the ultrasound image U and the view image C synchronized with each other together on the terminal monitor 36 as shown in FIG. 3. For this reason, the operator can simultaneously confirm the position of the ultrasound probe 2 and a state of the tissue in the subject corresponding thereto.

Similarly, the image synchronization unit 43 of the external apparatus 4 can send each of the ultrasound image U and the view image C synchronized with each other to the display controller 44, instead of generating the composite image M. Even in this case, since the ultrasound image U and the view image C synchronized with each other are simultaneously displayed on the external monitor 45, the observer who observes the external monitor 45 can observe the view image C and the ultrasound image U captured in a site of inspection where the subject and the operator are positioned, substantially in real time.

Although the ultrasound probe 2 and the mobile information terminal 3 are connected to each other by wireless communication, for example, the ultrasound probe 2 and the mobile information terminal 3 may be connected to each other by wired communication, instead of being connected by wireless communication.

In FIG. 4, although an example where the external apparatus 4 is a mobile thin type computer, such as a so-called smartphone or a tablet, like the mobile information terminal 3 has been illustrated, the external apparatus 4 is not limited thereto. For example, as the external apparatus 4, a so-called notebook type personal computer, a stationary type personal computer, or the like may be used.

Though not shown, a second external apparatus having a monitor may be provided close to a site where the subject is inspected by the operator, the second external apparatus may be connected to the ultrasound probe 2 and the mobile information terminal 3, and the ultrasound image U and the view image C may be displayed on the monitor of the second external apparatus. In particular, in a case where the second external apparatus has a large monitor, since the operator can more clearly confirm the ultrasound image U and the view image C, the operator can clearly correspond and recognize the scanning point of the ultrasound probe 2 in the subject and the tissue in the subject to be observed.

In FIG. 3, although an example where the mobile information terminal 3 is a mobile thin type computer, such as a so-called smartphone or a tablet has been illustrated, the mobile information terminal 3 is not limited thereto, and any mobile information terminal may be used. For example, as the mobile information terminal 3, a terminal apparatus that is mountable on the head of the operator may be used. For example, the terminal monitor 36 is disposed to face the eyes of the operator in a state in which the terminal apparatus is mounted on the head, and the view image C representing a field of view in front of the operator is captured by the camera unit 33. The operator can indirectly confirm the field of view in front of the operator by confirming the view image C displayed on the terminal monitor 36, instead of directly confirming the field of view in front of the operator. In this way, in a case where the mobile information terminal 3 is mounted on the head of the operator, since the operator does not need to hold the mobile information terminal 3 in a hand, for example, the operator can perform more various inspections, such as performing skill involving the hands to insert a so-called puncture needle into the subject using the other hand while operating the ultrasound probe 2 using one hand.

As shown in FIG. 2, although the transmission and reception circuit 22 has the beamformer 54 together with the amplification unit 52 and the AD conversion unit 53, the beamformer 54 may be disposed between the transmission and reception circuit 22 and the signal processing unit 23, not inside the transmission and reception circuit 22. In this case, the probe-side processor 27 may configure the beamformer 54.

In the ultrasound system 1 according to Embodiment 1 of the present invention, with the input of the probe freeze instruction through the input device 38 of the mobile information terminal 3 and the input of the probe freeze instruction through the input device 47 of the external apparatus 4, the transmission of the ultrasonic wave from the transducer array 21 of the ultrasound probe 2 and the imaging of the view image C by the camera unit 33 of the mobile information terminal 3 are stopped. In this case, instruction information transmission source information representing the guidance on the probe freeze instruction input from the input device 38 of the mobile information terminal 3 and the guidance on the probe freeze instruction input from the input device 47 of the external apparatus 4 can be displayed in the terminal monitor 36 of the mobile information terminal 3 and the external monitor 45 of the external apparatus 4.

Figure 5:
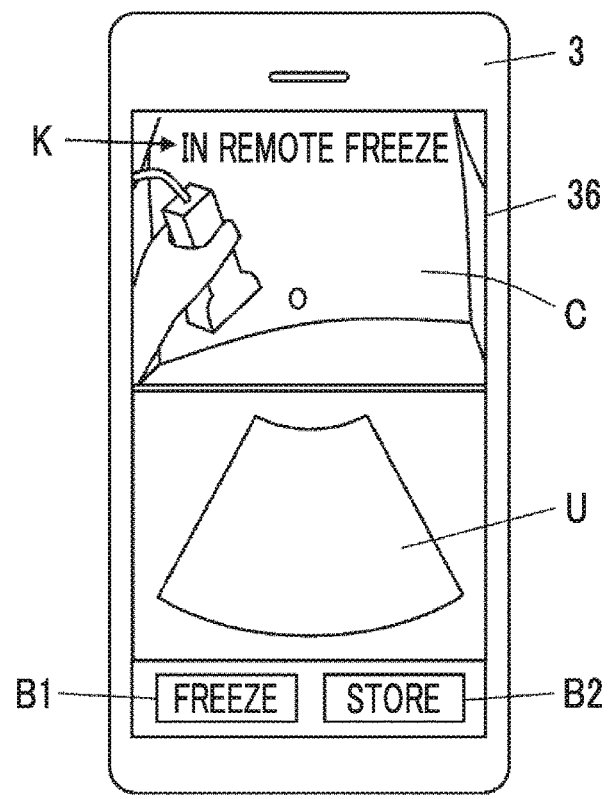
FIG. 5 is a diagram showing an example of a message representing that transmission of an ultrasonic wave is stopped, displayed on a terminal monitor in a modification example of Embodiment 1 of the present invention.

For example, in a case where the probe freeze instruction is input from the observer who observes the ultrasound image U and the view image C displayed on the external monitor 45, through the input device 47 of the external apparatus 4, as shown in FIG. 5, a message K representing the probe freeze instruction is input through the input device 47 of the external apparatus 4 can be displayed in the terminal monitor 36 of the mobile information terminal 3. In an example shown in FIG. 5, a message K "in remote freeze" is displayed on the terminal monitor 36. In this case, though not shown, the same message K as the message K displayed on the terminal monitor 36 is displayed even in the external monitor 45. For example, in a case where the probe freeze instruction is input from the operator of the ultrasound probe 2 and the mobile information terminal 3 through the input device 38 of the mobile information terminal 3, though not shown, a message K representing the probe freeze instruction is input through the input device 38 of the mobile information terminal 3, such as "in local freeze" is displayed in the terminal monitor 36 of the mobile information terminal 3 and the external monitor 45 of the external apparatus 4.

Figure 6:
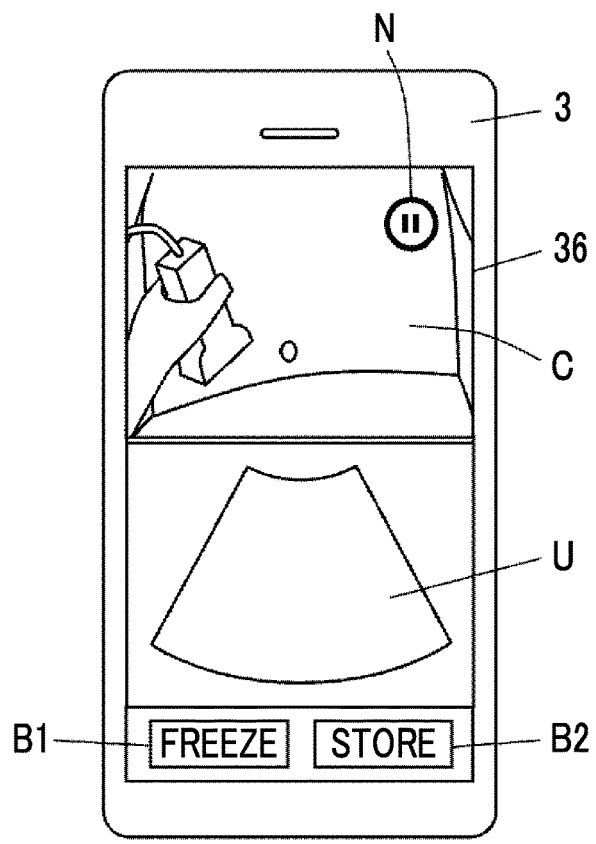
FIG. 6 is a diagram showing an example of a stop icon representing that the transmission of the ultrasonic wave is stopped, displayed on the terminal monitor in the modification example of Embodiment 1 of the present invention.

For example, in a case where the probe freeze instruction is input from the observer who observes the ultrasound image U and the view image C displayed on the external monitor 45 through the input device 47 of the external apparatus 4, as shown in FIG. 6, a stop icon N representing the probe freeze instruction is input through the input device 47 of the external apparatus 4 can be displayed in the terminal monitor 36 of the mobile information terminal 3. In this case, though not shown, the same stop icon N as the stop icon N displayed on the terminal monitor 36 is displayed even in the external monitor 45. For example, in a case where the probe freeze instruction is input from the operator of the ultrasound probe 2 and the mobile information terminal 3 through the input device 38 of the mobile information terminal 3, through not shown, a stop icon different from the stop icon N displayed in a case where the probe freeze instruction is input through the input device 47 of the external apparatus 4 is displayed in the terminal monitor 36 of the mobile information terminal 3 and the external monitor 45 of the external apparatus 4. Examples of such a stop icon include a stop icon having a shape, size, color, or the like different from the stop icon N displayed in a case where the probe freeze instruction is input through the input device 47 of the external apparatus 4.

Figure 7:
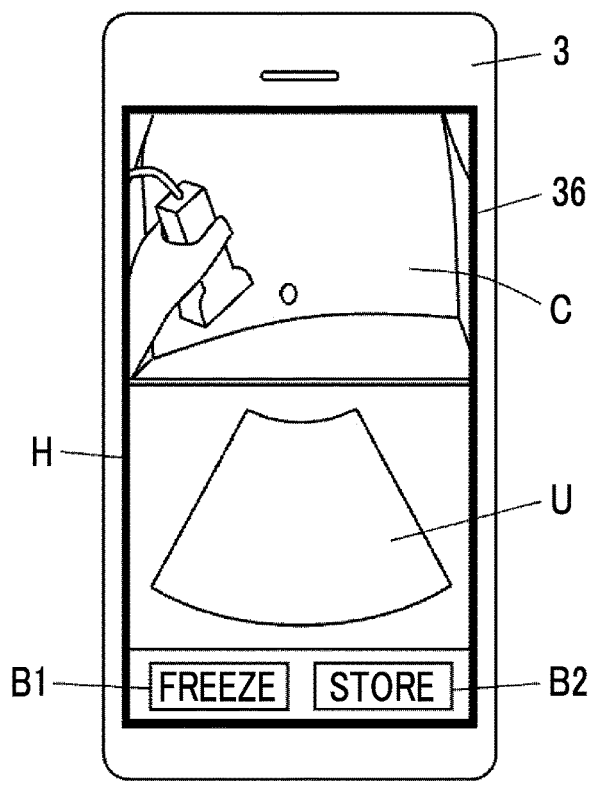
FIG. 7 is a diagram showing a frame line representing that the transmission of the ultrasonic wave is stopped, displayed on the terminal monitor in the modification example of Embodiment 1 of the present invention.

For example, in a case where the probe freeze instruction is input from the observer who observes the ultrasound image U and the view image C displayed on the external monitor 45 through the input device 47 of the external apparatus 4, as shown in FIG. 7, a frame line H representing that the probe freeze instruction is input through the input device 47 of the external apparatus 4 can be displayed in the terminal monitor 36 of the mobile information terminal 3. In this case, though not shown, the same frame line H as the frame line H displayed on the terminal monitor 36 is displayed even in the external monitor 45. For example, in a case where the probe freeze instruction is input from the operator of the ultrasound probe 2 and the mobile information terminal 3 through the input device 38 of the mobile information terminal 3, through not shown, a frame line different from the frame line displayed in a case where the probe freeze instruction is input through the input device 47 of the external apparatus 4 is displayed in the terminal monitor 36 of the mobile information terminal 3 and the external monitor 45 of the external apparatus 4. Examples of such a frame line include a frame line having a shape, size, thickness, color, or the like different from the frame line displayed in a case where the probe freeze instruction is input through the input device 47 of the external apparatus 4.

In this manner, the instruction information transmission source information representing from which of the input device 38 of the mobile information terminal 3 and the input device 47 of the external apparatus 4 the probe freeze instruction is input is displayed in the terminal monitor 36 of the mobile information terminal 3 and the external monitor 45 of the external apparatus 4, whereby the operator of the ultrasound probe 2 and the mobile information terminal 3 and the observer who views the external monitor 45 can easily recognize from which of the mobile information terminal 3 side and the external apparatus 4 side the probe freeze instruction is input. In particular, even in a case where the display of the ultrasound image U and the view image C is suddenly temporarily stopped in the terminal monitor 36 of the mobile information terminal 3 with the input of the probe freeze instruction through the input device 47 of the external apparatus 4, the operator of the ultrasound probe 2 and the mobile information terminal 3 can easily recognize that the probe freeze instruction is input through the input device 47 of the external apparatus 4 and can perform an operation to store the ultrasound image U and the view image C the display of which is temporarily stopped, or the like without confusion.

For example, in a state in which the transmission of the ultrasonic wave from the transducer array 21 and the imaging of the view image C by the camera unit 33 are stopped and the display of the ultrasound image U and the view image C is temporarily stopped in the terminal monitor 36 and the external monitor 45, with an input operation of the operator through the input device 38 of the mobile information terminal 3 and an input operation of the observer through the input device 47 of the external apparatus 4, the stop of the transmission of the ultrasonic wave from the transducer array 21 and the stop of the imaging of the view image C by the camera unit 33 can be released, and the ultrasound image U and the view image C can be continuously displayed again in the terminal monitor 36 and the external monitor 45.

For example, as shown in FIGS. 3 and 4, in a case where a freeze button B1 is displayed on the terminal monitor 36 of the mobile information terminal 3 and the external monitor 45 of the external apparatus 4, with a touch of the operator on the freeze button B1 displayed on the terminal monitor 36 or a touch of the observer on the freeze button B1 displayed on the external monitor 45 as a trigger, the transmission of the ultrasonic wave from the transducer array 21 and the imaging of the view image C by the camera unit 33 can be stopped, and the display of the ultrasound image U and the view image C can be temporarily stopped in the terminal monitor 36 and the external monitor 45. In a state in which the display of the ultrasound image U and the view image C is temporarily stopped in the terminal monitor 36 and the external monitor 45, as the freeze button B1 displayed on the terminal monitor 36 or the freeze button B1 displayed on the external monitor 45 is touched again, the stop of the transmission of the ultrasonic wave from the transducer array 21 and the stop of the imaging of the view image C by the camera unit 33 can be released, and the display of the ultrasound image U and the view image C can be continuously displayed again in the terminal monitor 36 and the external monitor 45.

In this way, the freeze button B1 displayed on the terminal monitor 36 and the freeze button B1 displayed on the external monitor 45 can be used as a release button for releasing the stop of the transmission of the ultrasonic wave from the transducer array 21 and the stop of the imaging of the view image C by the camera unit 33.

For example, in a case where the instruction information transmission source information, such as the message K shown in FIG. 5 or the stop icon N shown in FIG. 6, representing from which of the input device 38 of the mobile information terminal 3 and the input device 47 of the external apparatus 4 the probe freeze instruction is input is displayed in the terminal monitor 36 and the external monitor 45, with a touch of the operator on the instruction information transmission source information displayed on the terminal monitor 36 or a touch of the observer on the instruction information transmission source information displayed on the external monitor 45 as a trigger, the stop of the transmission of the ultrasonic wave from the transducer array 21 and the stop of the imaging of the view image C by the camera unit 33 can be released, and the display of the ultrasound image U and the view image C can be continuously displayed again in the terminal monitor 36 and the external monitor 45.

Figure 8:
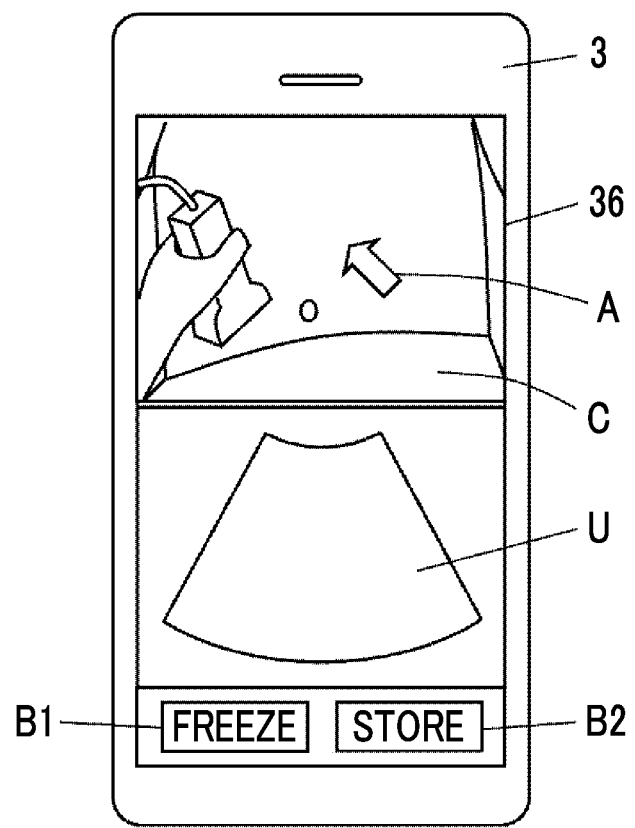
FIG. 8 is a diagram schematically showing an example of a cursor disposed on a view image in another modification example of Embodiment 1 of the present invention.

For example, as shown in FIG. 8, external input information, such as a cursor A that is movable by an input operation of the observer through the input device 47 of the external apparatus 4, can be displayed on the external monitor 45 of the external apparatus 4 and the terminal monitor 36 of the mobile information terminal 3 simultaneously. In this case, for example, in a case where the cursor A displayed on the external monitor 45 of the external apparatus 4 is moved by an input operation of the observer through the input device 47 of the external apparatus 4, the cursor A displayed on the terminal monitor 36 of the mobile information terminal 3 is moved similarly. With this, for example, it is possible to perform more detailed information sharing between the operator of the ultrasound probe 2 and the mobile information terminal 3 and the observer positioned close to the external apparatus 4. For example, the observer having a high level of skill who observes the ultrasound image U and the view image C on the external monitor 45 of the external apparatus 4 can easily support inspection that is performed by the operator, such as indicating a position where the ultrasound probe 2 is to be scanned, to the operator having a low level of skill of the ultrasound probe 2 and the mobile information terminal 3 using the cursor A.

For example, the cursor A that is movable by an input operation of the operator through the input device 38 of the mobile information terminal 3 may be displayed on the terminal monitor 36 of the mobile information terminal 3 and the external monitor 45 of the external apparatus 4 simultaneously. In this case, for example, the operator having a high level of skill can perform training on ultrasound diagnosis for the observer having a low level of skill positioned close to the external apparatus 4 more easily and in more detail.

The shape of the cursor A is not limited to an arrow shape, and can have any shape, such as a circular shape or a polygonal shape.

Figure 9:
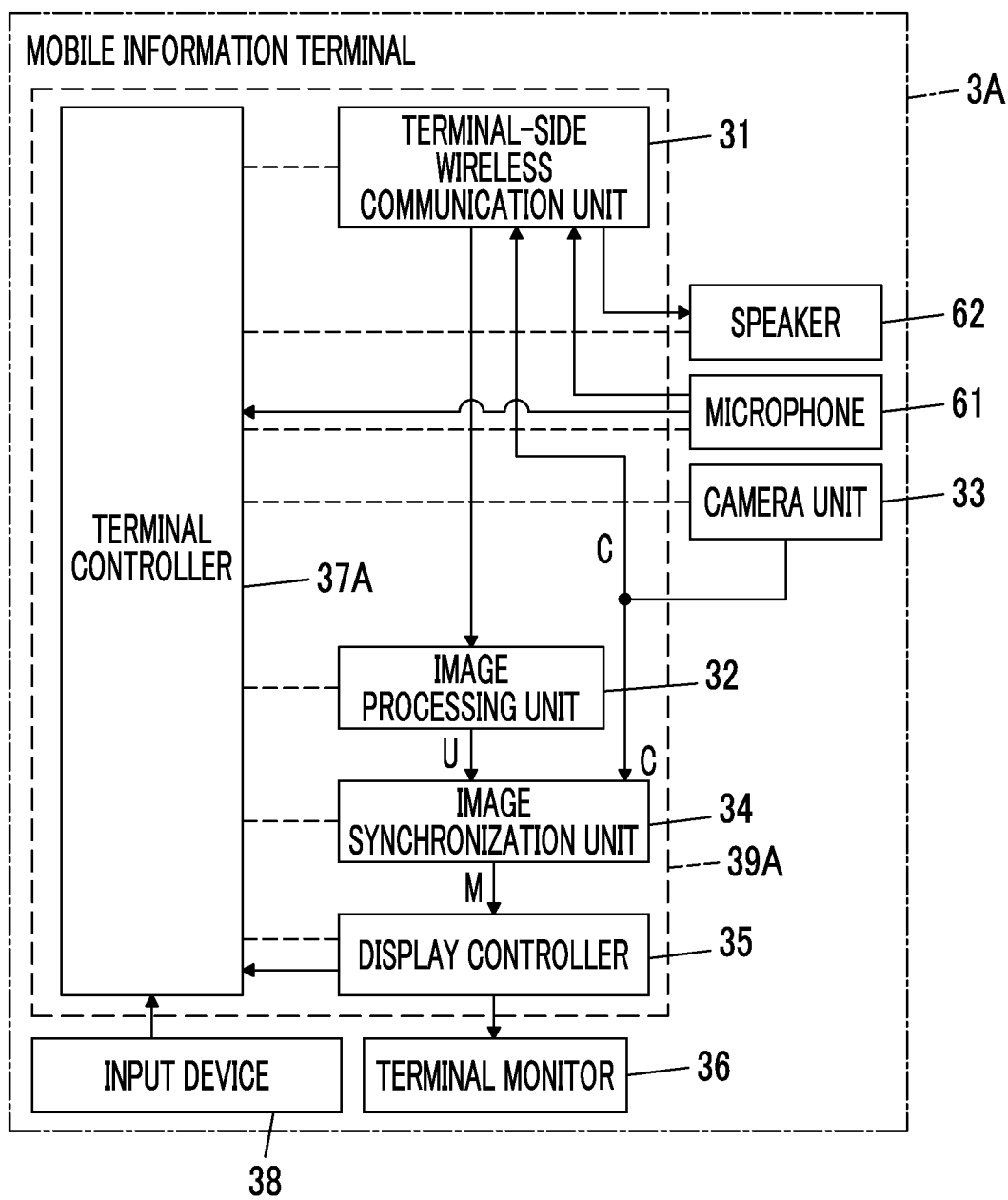
FIG. 9 is a block diagram showing the configuration of a mobile information terminal in still another modification example of Embodiment 1 of the present invention.

For example, wireless communication of voice data may be performed between the mobile information terminal 3 and the external apparatus 4 in two directions. FIG. 9 shows the configuration of a mobile information terminal 3A in a modification example of Embodiment 1 of the present invention. The mobile information terminal 3A is further provided with a microphone 61 and a speaker 62, comprises a terminal controller 37A instead of the terminal controller 37, and comprises a terminal-side processor 39A instead of the terminal-side processor 39, compared to the mobile information terminal 3 shown in FIG. 1. In the mobile information terminal 3A, the microphone 61 and the speaker 62 are connected to the terminal-side wireless communication unit 31.

Figure 10:
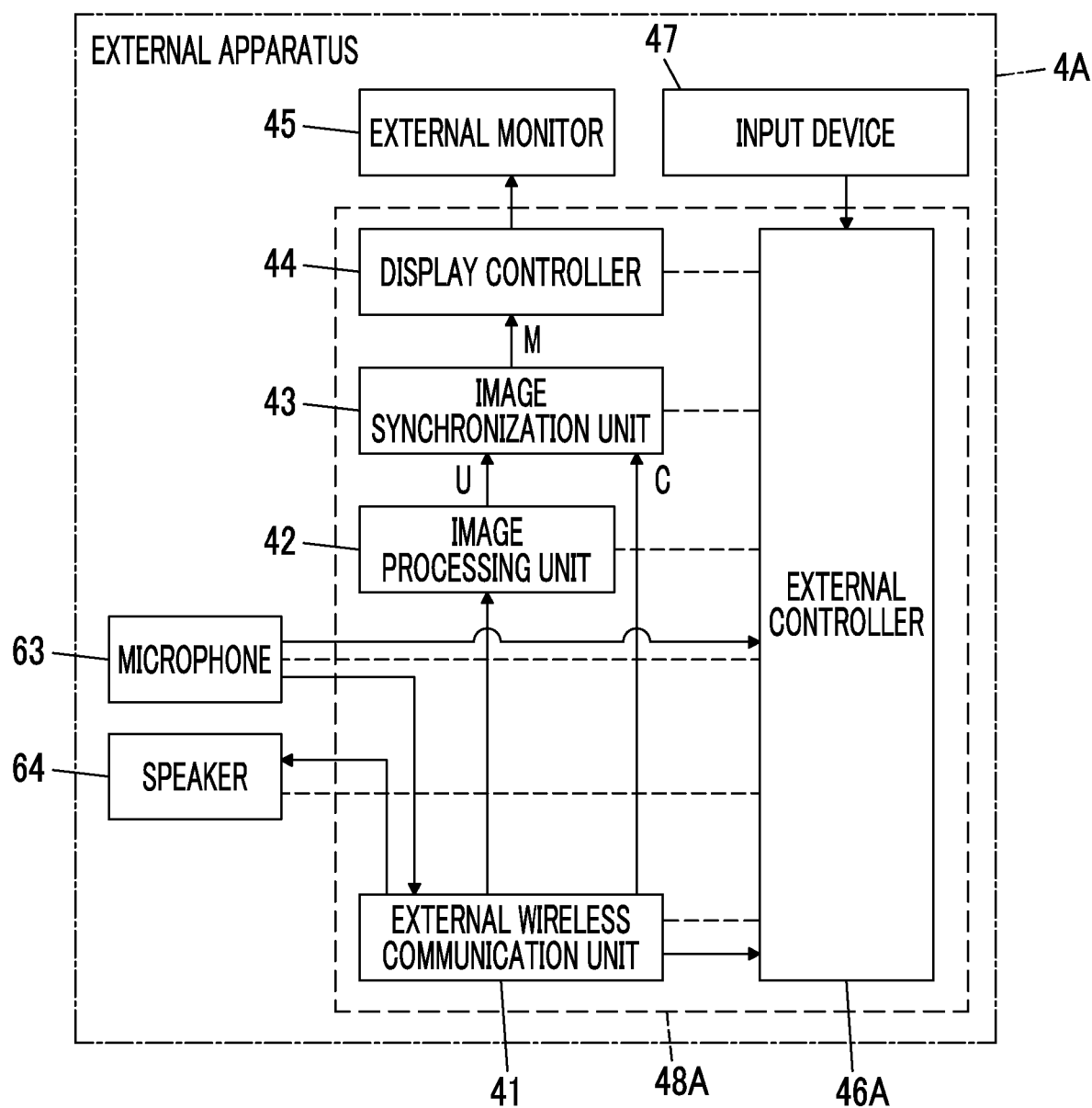
FIG. 10 is a block diagram showing the configuration of an external apparatus in still another modification example of Embodiment 1 of the present invention.

FIG. 10 shows the configuration of an external apparatus 4A in the modification example of Embodiment 1 of the present invention. The external apparatus 4A is further provided with a microphone 63 and a speaker 64, comprises an external controller 46A instead of the external controller 46, and comprises an external apparatus-side processor 48A instead of the external apparatus-side processor 48, compared to the external apparatus 4 shown in FIG. 1. In the external apparatus 4A, the microphone 63 and the speaker 64 are connected to the external wireless communication unit 41.

In the modification example of Embodiment 1 of the present invention, voice data is transmitted and received between the mobile information terminal 3A and the external apparatus 4A in two directions. For example, in a case where the operator of the ultrasound probe 2 and the mobile information terminal 3A utters voice toward the mobile information terminal 3A, the uttered voice is input to the microphone 61 of the mobile information terminal 3A, and voice data is generated by the microphone 61. The generated voice data is wirelessly transmitted from the terminal-side wireless communication unit 31 to the external apparatus 4A. The external wireless communication unit 41 of the external apparatus 4A receives the voice data wirelessly transmitted from the mobile information terminal 3A and sends the received voice data to the speaker 64. The speaker 64 reproduces the voice uttered by the operator of the ultrasound probe 2 and the mobile information terminal 3A based on the voice data received from the external wireless communication unit 41.

For example, the observer who observes the ultrasound image U and the view image C on the external monitor 45 of the external apparatus 4A utters voice toward the external apparatus 4A, the uttered voice is input to the microphone 63 of the external apparatus 4A, and voice data is generated by the microphone 63. The generated voice data is wirelessly transmitted from the external wireless communication unit 41 to the mobile information terminal 3A. The terminal-side wireless communication unit 31 of the mobile information terminal 3A receives the voice data wirelessly transmitted from the external apparatus 4A and sends the received voice data to the speaker 62. The speaker 62 reproduces the voice uttered by the observer positioned close to the external apparatus 4 based on the voice data received from the terminal-side wireless communication unit 31.

In this manner, the voice data is transmitted and received between the mobile information terminal 3A and the external apparatus 4A in two directions, whereby it is possible to perform more detailed information sharing between the operator of the ultrasound probe 2 and the mobile information terminal 3A and the observer positioned close to the external apparatus 4A. For example, the observer having a high level of skill who observes the ultrasound image U and the view image C on the external monitor 45 of the external apparatus 4A can give advice to the operator having a low level of skill of the ultrasound probe 2 and the mobile information terminal 3A more easily and in more detail. For example, the operator having a high level of skill can perform training on ultrasound diagnosis for the observer having a low level of skill positioned close to the external apparatus 4A more easily and in more detail.

The voice of the operator input to the microphone 61 of the mobile information terminal 3A may be used as an input operation of the operator. For example, the terminal controller 37A can acquire instruction information by analyzing the voice data generated based on the voice of the operator by the microphone 61 and can perform control of each unit of the mobile information terminal 3A, such as imaging start and imaging stop of the view image C by the camera unit 33, conforming to the acquired instruction information. Alternatively, the control of the ultrasound probe 2 may be performed based on the voice data analyzed by the terminal controller 37A. In this case, for example, the voice data analyzed by the terminal controller 37A is wirelessly transmitted as input information from the operator from the terminal-side wireless communication unit 31 to the ultrasound probe 2, and is input to the probe controller 26 by way of the probe-side wireless communication unit 24. The probe controller 26 can perform control of each unit of the ultrasound probe 2, such as transmission start and transmission stop of ultrasonic waves by the transducer array 21.

Alternatively, the voice of the observer input to the microphone 63 of the external apparatus 4A may be used as an input operation of the observer. For example, the external controller 46A may acquire instruction information by analyzing the voice data generated based on the voice of the observer by the microphone 63 and may perform control of each unit of the mobile information terminal 3A, such as imaging start and imaging stop of the view image C by the camera unit 33 of the mobile information terminal 3A, and control of each unit of the ultrasound probe 2, such as transmission start and transmission stop of ultrasonic waves by the transducer array 21 of the ultrasound probe 2.

Embodiment 2

In Embodiment 1, although the reception data before imaging obtained by performing the envelope detection processing on the sound ray signal is generated in the ultrasound probe 2, and the generated reception data before imaging is wirelessly transmitted to the mobile information terminal 3 and the external apparatus 4, the ultrasound image U may be generated in the ultrasound probe 2, and the generated ultrasound image U may be wirelessly transmitted to the mobile information terminal 3 and the external apparatus 4.

Figure 11:
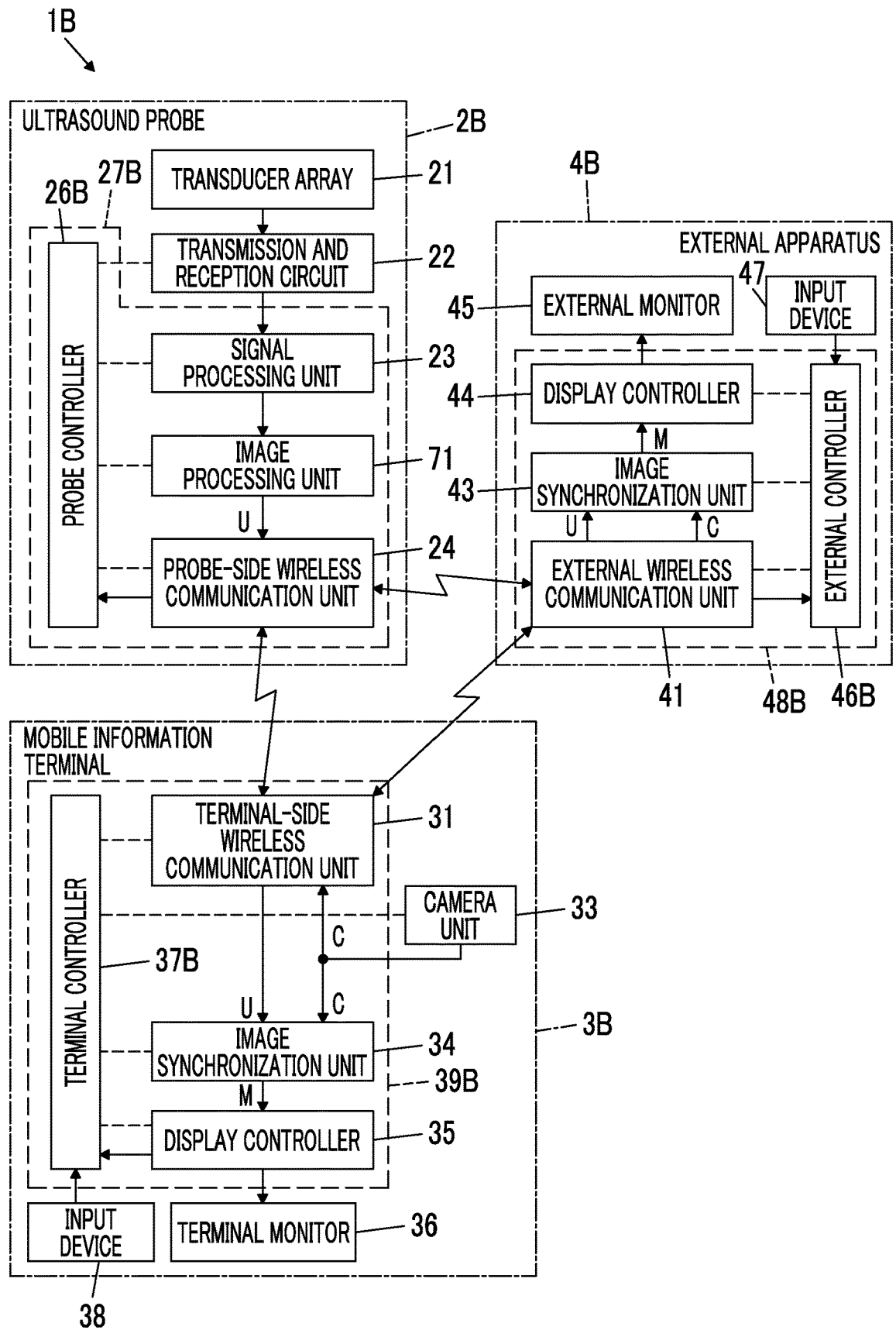
FIG. 11 is a block diagram showing the configuration of an ultrasound system according to Embodiment 2 of the present invention.

FIG. 11 shows the configuration of an ultrasound system 1B according to Embodiment 2 of the present invention. The ultrasound system 1B comprises an ultrasound probe 2B instead of the ultrasound probe 2, comprises a mobile information terminal 3B instead of the mobile information terminal 3, and comprises an external apparatus 4B instead of the external apparatus 4, compared to the ultrasound system 1 of Embodiment 1 shown in FIG. 1.

The ultrasound probe 2B is further provided with an image processing unit 71, comprises a probe controller 26B instead of the probe controller 26, and a probe-side processor 27B instead of the probe-side processor 27, compared to the ultrasound probe 2 in Embodiment 1. In the ultrasound probe 2B, the image processing unit 71 is connected to the signal processing unit 23. Though not shown, the signal processing unit 23 and the image processing unit 71 configure an ultrasound image generation unit. The probe-side wireless communication unit 24 and the probe controller 26B are connected to the image processing unit 71.

The mobile information terminal 3B is not provided with the image processing unit 32, comprises a terminal controller 37B instead of the terminal controller 37, and comprises a terminal-side processor 39B instead of the terminal-side processor 39, compared to the mobile information terminal 3 in Embodiment 1. In the mobile information terminal 3B, the image synchronization unit 34 and the camera unit 33 are connected to the terminal-side wireless communication unit 31.

The external apparatus 4B is not provided with the image processing unit 42, comprises an external controller 46B instead of the external controller 46, and comprises an external apparatus-side processor 48B instead of the external apparatus-side processor 48, compared to the external apparatus 4 in Embodiment 1.

The image processing unit 71 of the ultrasound probe 2B raster-converts the signal subjected to the envelope detection processing by the signal processing unit 23 into an image signal conforming to a normal television signal scanning system and executes various kinds of necessary image processing, such as brightness correction, gradation correction, sharpness correction, an image size correction, refresh rate correction, scanning frequency correction, and color correction, on the converted image signal, thereby generating an ultrasound image U conforming to a display format for the terminal monitor 36 of the mobile information terminal 3B and an ultrasound image U conforming to a display format for the external monitor 45 of the external apparatus 4B. The image processing unit 71 wirelessly transmits the ultrasound image U conforming to the display format for the terminal monitor 36 of the mobile information terminal 3B from the probe-side wireless communication unit 24 to the mobile information terminal 3B and wirelessly transmits the ultrasound image U conforming to the display format for the external monitor 45 of the external apparatus 4B from the probe-side wireless communication unit 24 to the external apparatus 4B.

The terminal-side wireless communication unit 31 of the mobile information terminal 3B receives the ultrasound image U wirelessly transmitted from the ultrasound probe 2B and sends the received ultrasound image U to the image synchronization unit 34.

The image synchronization unit 34 synchronizes the ultrasound image U sent from the terminal-side wireless communication unit 31 and the view image C generated by the camera unit 33 with each other and generates a composite image M based on the ultrasound image U and the view image C synchronized with each other. For example, in a case where a time stamp representing a time at which the ultrasound image U is generated is given to the ultrasound image U by the image processing unit 71 of the ultrasound probe 2B, and a time stamp representing a time at which the view image C is generated is given to the view image C by the camera unit 33 of the mobile information terminal 3B, the image synchronization unit 34 can synchronize the ultrasound image U and the view image C with each other based on the time stamps given to the ultrasound image U and the view image C.

The display controller 35 executes predetermined processing on the composite image M generated by the image synchronization unit 34, then, sends the composite image M to the terminal monitor 36, and displays the ultrasound image U and the view image C synchronized with each other together on the terminal monitor 36 as shown in FIG. 3.

The external wireless communication unit 41 of the external apparatus 4B receives the ultrasound image U wirelessly transmitted from the ultrasound probe 2B and the view image C wirelessly transmitted from the mobile information terminal 3B and sends the received ultrasound image U and view image C to the image synchronization unit 43.

The image synchronization unit 43 synchronizes the ultrasound image U and the view image C sent from the external wireless communication unit 41 with each other and generates a composite image M based on the ultrasound image U and the view image C synchronized with each other.

The display controller 44 executes predetermined processing on the composite image M generated by the image synchronization unit 43, then, sends the composite image M to the external monitor 45, and displays the ultrasound image U and the view image C synchronized with each other together on the external monitor 45 as shown in FIG. 4.

As described above, with the ultrasound system 1B according to Embodiment 2 of the present invention, even in a case where the ultrasound probe 2B comprises the image processing unit 71, similarly to the ultrasound system 1 of Embodiment 1 in which the mobile information terminal 3 comprises the image processing unit 32 and the external apparatus 4 comprises the image processing unit 42, the same view image C and ultrasound image U are displayed on the terminal monitor 36 and the external monitor 45 substantially simultaneously. For this reason, for example, since the observer who observes the view image C and the ultrasound image U with the external apparatus 4B disposed at a remote location can give advice to the operator of the ultrasound probe 2B and the mobile information terminal 3B, an appropriate ultrasound image U is obtained, and it is possible to improve accuracy of ultrasound diagnosis.

In the ultrasound system 1B according to Embodiment 2 of the present invention, similarly to the ultrasound system 1 of Embodiment 1, as the observer who observes the ultrasound image U and the view image C displayed on the external monitor 45 input a probe freeze instruction through the input device 47 of the external apparatus 4B, the transmission of the ultrasonic wave from the transducer array 21 of the ultrasound probe 2B is stopped and the imaging of the view image C by the camera unit 33 of the mobile information terminal 3B is stopped, such that the display of the ultrasound image U and the view image C is temporarily stopped in the terminal monitor 36 of the mobile information terminal 3B and the external monitor 45 of the external apparatus 4B simultaneously.

For this reason, for example, even in a case where the level of the skill of the operator of the ultrasound probe 2B and the mobile information terminal 3B is low, and hardly determines whether or not an appropriate ultrasound image U is obtained, the observer having a high level of skill input the probe freeze instruction through the input device 47 of the external apparatus 4B, whereby the display of the ultrasound image U is temporarily stopped at an appropriate timing in the terminal monitor 36 and the external monitor 45. Accordingly, it is possible to obtain an appropriate ultrasound image U. With this, it is possible to improve accuracy of ultrasound diagnosis.

In the ultrasound system 1 of Embodiment 1 shown in FIG. 1, the mobile information terminal 3 comprises the image processing unit 32 and the external apparatus 4 comprises the image processing unit 42. In contrast, in the ultrasound system 1B according to Embodiment 2, the ultrasound probe 2B comprises the image processing unit 71. Thus, the mobile information terminal 3B and the external apparatus 4B do not need to have the image processing units 32 and 42, respectively, and the internal configurations of the mobile information terminal 3B and the external apparatus 4B are simplified compared to the internal configurations of the mobile information terminal 3 and the external apparatus 4 in the ultrasound system 1 of Embodiment 1. For this reason, with the ultrasound system 1B according to Embodiment 2, it is possible to reduce power consumption, calculation load, and the like of the mobile information terminal 3B and the external apparatus 4B, compared to the ultrasound system 1 of Embodiment 1.

Embodiment 3

In Embodiment 1, although the ultrasound image U and the view image C are synchronized in each of the mobile information terminal 3 and the external apparatus 4, for example, the ultrasound image U and the view image C may be synchronized only in the mobile information terminal 3.

Figure 12:
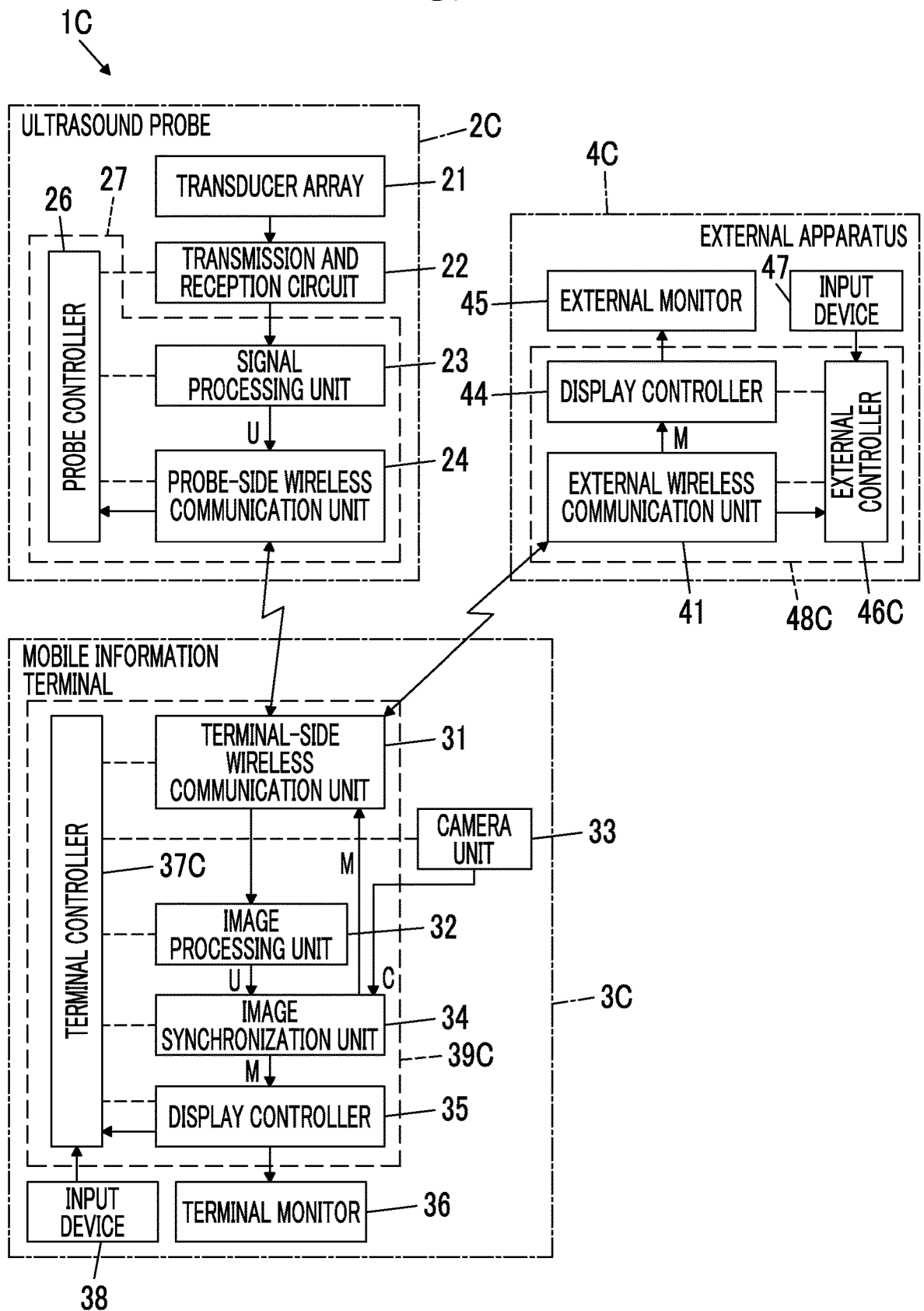
FIG. 12 is a block diagram showing the configuration of an ultrasound system according to Embodiment 3 of the present invention.

FIG. 12 shows the configuration of an ultrasound system 1C according to Embodiment 3 of the present invention. The ultrasound system 1C comprises an ultrasound probe 2C having the same internal configuration as the ultrasound probe 2, comprises a mobile information terminal 3C instead of the mobile information terminal 3, and comprises an external apparatus 4C instead of the external apparatus 4, compared to the ultrasound system 1 of Embodiment 1 shown in FIG. 1. The ultrasound probe 2C is connected only to the mobile information terminal 3C by wireless communication, and the external apparatus 4C is connected only to the mobile information terminal 3C by wireless communication.

The mobile information terminal 3C comprises a terminal controller 37C instead of the terminal controller 37 and comprises a terminal-side processor 39C instead of the terminal-side processor 39, compared to the mobile information terminal 3 in Embodiment 1. In the mobile information terminal 3C, the image synchronization unit 34 is connected to the terminal-side wireless communication unit 31. The camera unit 33 is connected to the image synchronization unit 34.

The external apparatus 4C is not provided with the image processing unit 42 and the image synchronization unit 43, comprises an external controller 46C instead of the external controller 46, and comprises an external apparatus-side processor 48C instead of the external apparatus-side processor 48, compared to the external apparatus 4 in Embodiment 1. In the external apparatus 4C, the display controller 44 is connected to the external wireless communication unit 41.

The probe-side wireless communication unit 24 of the ultrasound probe 2C wirelessly transmits the reception data before imaging subjected to the envelope detection processing by the signal processing unit 23 only to the mobile information terminal 3C.

The terminal-side wireless communication unit 31 of the mobile information terminal 3C receives the reception data before imaging wirelessly transmitted from the ultrasound probe 2C and sends the received reception data before imaging to the image processing unit 32.

The image processing unit 32 raster-converts the reception data before imaging sent from the terminal-side wireless communication unit 31 into an image signal conforming to a normal television signal scanning system and executes various kinds of necessary image processing, such as brightness correction, gradation correction, sharpness correction, an image size correction, refresh rate correction, scanning frequency correction, and color correction, on the converted image signal, thereby generating an ultrasound image U conforming to the display format for the terminal monitor 36 of the mobile information terminal 3C and an ultrasound image U conforming to a display format for the external monitor 45 of the external apparatus 4B. The image processing unit 32 sends the ultrasound image U conforming to the display format for the terminal monitor 36 of the mobile information terminal 3C and the ultrasound image U conforming to the display format for the external monitor 45 of the external apparatus 4B to the image synchronization unit 34.

The camera unit 33 acquires a view image C obtained by a scanning point of the ultrasound probe 2C in the subject and sends the acquired view image C to the image synchronization unit 34.

The image synchronization unit 34 synchronizes the ultrasound image U sent from the image processing unit 32 and the view image C sent from the camera unit 33 with each other. More specifically, the image synchronization unit 34 synchronizes the ultrasound image U conforming to the display format for the terminal monitor 36 of the mobile information terminal 3C and the view image C with each other to generate a composite image M, and synchronizes the ultrasound image U conforming to the display format for the external monitor 45 of the external apparatus 4C and the view image C with each other to generate a composite image M.

The image synchronization unit 34 sends the composite image M generated based on the ultrasound image U conforming to the display format for the terminal monitor 36 of the mobile information terminal 3C and the view image C synchronized with each other on the display controller 35. The display controller 35 executes predetermined processing on the composite image M sent from the image synchronization unit 34, then, sends the composite image M to the terminal monitor 36, and displays the ultrasound image U and the view image C synchronized with each other together on the terminal monitor 36 as shown in FIG. 3. The image synchronization unit 34 sends the composite image M generated based on the ultrasound image U conforming to the display format for the external monitor 45 of the external apparatus 4C and the view image C to the terminal-side wireless communication unit 31.

The terminal-side wireless communication unit 31 wirelessly transmits the composite image M sent from the image synchronization unit 34 to the external apparatus 4C.

The external wireless communication unit 41 of the external apparatus 4C receives the composite image M wirelessly transmitted from the mobile information terminal 3C and sends the received composite image M to the display controller 44. The display controller 44 executes predetermined processing on the composite image M sent from the external wireless communication unit 41, then, sends the composite image M to the external monitor 45, and displays the ultrasound image U and the view image C synchronized with each other together on the external monitor 45 as shown in FIG. 4.

The probe freeze instruction input from the observer who observes the ultrasound image U and the view image C displayed on the external monitor 45 through the input device 47 of the external apparatus 4C is sent to the external wireless communication unit 41 by way of the external controller 46C. The external wireless communication unit 41 wirelessly transmits the probe freeze instruction only to the terminal-side wireless communication unit 31 of the mobile information terminal 3C. The terminal-side wireless communication unit 31 inputs the probe freeze instruction wirelessly transmitted from the external wireless communication unit 41 of the external apparatus 4C to the terminal controller 37C and wirelessly transmits the probe freeze instruction to the probe controller 26 of the ultrasound probe 2C.

The terminal controller 37C of the mobile information terminal 3C performs control such that the camera unit 33 stops the generation of the view image C, with the input of the probe freeze instruction as a trigger. The probe-side wireless communication unit 24 of the ultrasound probe 2C inputs the probe freeze instruction wirelessly transmitted from the terminal-side wireless communication unit 31 of the mobile information terminal 3C to the probe controller 26. The probe controller 26 performs control such that the transmission and reception circuit 22 stops the transmission of the ultrasonic wave from the transducer array 21, in response to the probe freeze instruction.

With this, the transmission of the ultrasonic wave from the transducer array 21 and the imaging of the view image C by the camera unit 33 are stopped, and the display of the ultrasound image U and the view image C is temporarily stopped in the terminal monitor 36 and the external monitor 45.

From the above description, with the ultrasound system 1C according to Embodiment 3 of the present invention, even in a case where only the mobile information terminal 3C comprises the image processing unit 32 and the image synchronization unit 34, similarly to the ultrasound system 1 of Embodiment 1 in which the mobile information terminal 3 comprises the image processing unit 32 and the external apparatus 4 comprises the image processing unit 42, the same view image C and ultrasound image U are displayed on the terminal monitor 36 and the external monitor 45 substantially simultaneously. For this reason, for example, since the observer who observes the view image C and the ultrasound image U with the external apparatus 4C disposed at a remote location can give advice to the operator of the ultrasound probe 2C and the mobile information terminal 3C, an appropriate ultrasound image U is obtained, and it is possible to improve accuracy of ultrasound diagnosis.

In the ultrasound system 1C according to Embodiment 3 of the present invention, similarly to the ultrasound system 1 of Embodiment 1, as the observer who observes the ultrasound image U and the view image C displayed on the external monitor 45 inputs the probe freeze instruction through the input device 47 of the external apparatus 4C, the transmission of the ultrasonic wave from the transducer array 21 of the ultrasound probe 2C is stopped and the imaging of the view image C by the camera unit 33 of the mobile information terminal 3C is stopped, such that the display of the ultrasound image U and the view image C is temporarily stopped in the terminal monitor 36 of the mobile information terminal 3C and the external monitor 45 of the external apparatus 4C.

For this reason, for example, even in a case where the level of skill of the operator of the ultrasound probe 2C and the mobile information terminal 3C is low and hardly determines whether or not an appropriate ultrasound image U is obtained, the observer having a high level of skill inputs the probe freeze instruction through the input device 47 of the external apparatus 4C, whereby the display of the ultrasound image U is temporarily stopped at an appropriate timing in the terminal monitor 36 and the external monitor 45. Accordingly, it is possible to obtain an appropriate ultrasound image U. With this, it is possible to improve accuracy of ultrasound diagnosis.

In the ultrasound system 1 of Embodiment 1 shown in FIG. 1, the external apparatus 4 comprises the image processing unit 42 and the image synchronization unit 43. In contrast, in the ultrasound system 1C according to Embodiment 3, the composite image M generated based on the ultrasound image U and the view image C is wirelessly transmitted from the mobile information terminal 3C to the external apparatus 4C. Thus, the external apparatus 4C does not need to have the image processing unit 42 and the image synchronization unit 43, and the internal configuration of the external apparatus 4C is simplified compared to the internal configuration of the external apparatus 4 in Embodiment 1. For this reason, with the ultrasound system 1C according to Embodiment 3, it is possible to reduce power consumption, calculation load, and the like of the external apparatus 4C.

In a case where the display of the ultrasound image U and the view image C is temporarily stopped in the external monitor 45 of the external apparatus 4C and the terminal monitor 36 of the mobile information terminal 3C with the input of the probe freeze instruction through the input device 47 of the external apparatus 4C, deviation may occur between a timing at which the display of the ultrasound image U and the view image C is temporarily stopped in the external monitor 45 and a timing at which the display of the ultrasound image U and the view image C is temporarily stopped in the terminal monitor 36, depending on a wireless communication state between the external apparatus 4C and the mobile information terminal 3C. In this case, for example, the ultrasound image U and the view image C corresponding to the time earlier by several frames from the ultrasound image U and the view image C displayed in a temporarily stopped state in the terminal monitor 36 may be displayed in a temporarily stopped state in the external monitor 45.

In this case, for example, the ultrasound image U and the view image C displayed in the temporarily stopped state in the terminal monitor 36 and the ultrasound image U and the view image C displayed in the temporarily stopped state in the external monitor 45 can be regarded as the substantially same images, respectively, and the ultrasound image U and the view image C displayed in each of the temporarily stopped state in the terminal monitor 36 and the external monitor 45 can be continuously displayed without change.

For example, the mobile information terminal 3C may comprise a memory (not shown) that stores the composite image M generated based on the ultrasound image U and the view image C synchronized with each other, and the same ultrasound image U and view image C as the ultrasound image U and the view image C displayed in the temporarily stopped state in the external monitor 45 may be called and displayed on the terminal monitor 36.

For example, in a case where the ultrasound probe 2C, the mobile information terminal 3C, and the external apparatus 4C are connected to one another by wireless communication using 5th Generation mobile communication system, called 5th Generation, and a frame rate for displaying the ultrasound image U and the view image C in the terminal monitor 36 and the external monitor 45 is set to 30 Hz, a time required for transmission and reception of the probe freeze instruction between the ultrasound probe 2C, and the mobile information terminal 3C and the external apparatus 4C is about 1 ms or less. In this case, it is considered that the deviation between the timing at which the display of the ultrasound image U and the view image C is temporarily stopped in the external monitor 45 and the timing at which the display of the ultrasound image U and the view image C is temporarily stopped in the terminal monitor 36 is a maximum of about one frame. For this reason, in a case where the deviation occurs between the timing at which the display of the ultrasound image U and the view image C is temporarily stopped in the external monitor 45 and the timing at which the display of the ultrasound image U and the view image C is temporarily stopped in the terminal monitor 36, the ultrasound image U and the view image C corresponding to the time earlier by one frame are called from the memory (not shown) of the mobile information terminal 3C and displayed on the terminal monitor 36, whereby the same ultrasound image U and view image C as the ultrasound image U and the view image C displayed in the temporarily stopped state in the external monitor 45 can be displayed on the terminal monitor 36.

For example, the ultrasound image U and the view image C displayed in the temporarily stopped state on the external monitor 45 may be wirelessly transmitted from the external wireless communication unit 41 to the terminal-side wireless communication unit 31 of the mobile information terminal 3C, and the ultrasound image U and the view image C wirelessly transmitted from the external wireless communication unit 41 may be displayed on the terminal monitor 36 through the display controller 35 of the mobile information terminal 3C. With this, the same ultrasound image U and view image C can be displayed in the terminal monitor 36 and the external monitor 45.

Embodiment 4

In Embodiment 3, although the reception data before imaging subjected to the envelope detection processing by the signal processing unit 23 of the ultrasound probe 2 is wirelessly transmitted to the mobile information terminal 3 and the external apparatus 4, the ultrasound image U may be generated in the ultrasound probe 2.

Figure 13:
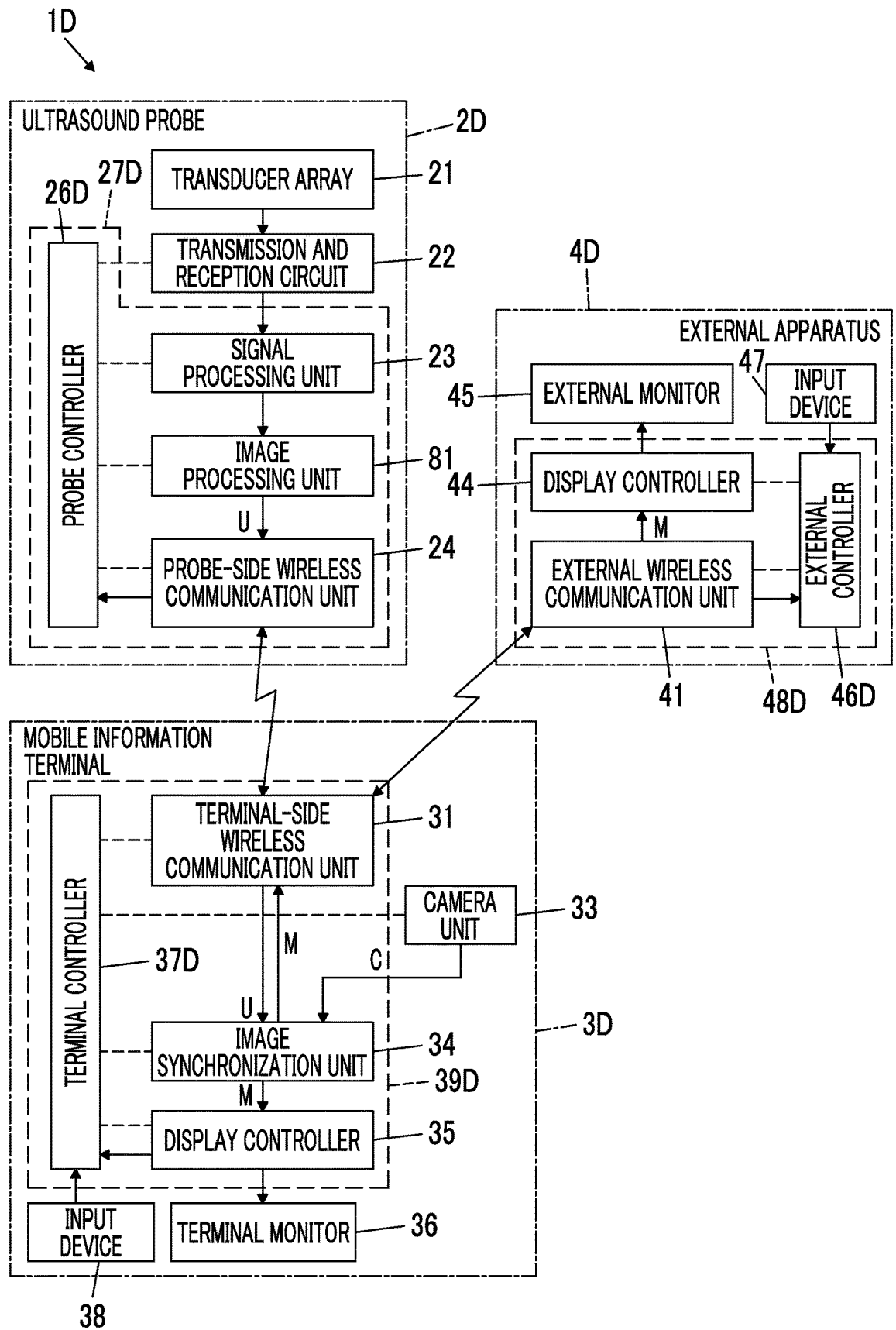
FIG. 13 is a block diagram showing the configuration of an ultrasound system according to Embodiment 4 of the present invention.

FIG. 13 shows the configuration of an ultrasound system 1D according to Embodiment 4 of the present invention. The ultrasound system 1D comprises an ultrasound probe 2D instead of the ultrasound probe 2C, comprises a mobile information terminal 3D instead of the mobile information terminal 3C, and comprises an external apparatus 4D instead of the external apparatus 4C, compared to the ultrasound system 1C of Embodiment 3 shown in FIG. 12. The ultrasound probe 2D is connected only to the mobile information terminal 3D by wireless communication, and the external apparatus 4D is connected only to the mobile information terminal 3D by wireless communication.

The ultrasound probe 2D is further provided with an image processing unit 81, comprises a probe controller 26D instead of the probe controller 26, and comprises a probe-side processor 27D instead of the probe-side processor 27, compared to the ultrasound probe 2C in Embodiment 3. In the ultrasound probe 2D, the image processing unit 81 is connected to the signal processing unit 23, and the probe-side wireless communication unit 24 and the probe controller 26D are connected to the image processing unit 81. Though not shown, the signal processing unit 23 and the image processing unit 81 configure an ultrasound image generation unit.

The mobile information terminal 3D is not provided with the image processing unit 32, comprises a terminal controller 37D instead of the terminal controller 37C, and comprises a terminal-side processor 39D instead of the terminal-side processor 39C, compared to the mobile information terminal 3C in Embodiment 3. In the mobile information terminal 3D, the image synchronization unit 34 is connected to the terminal-side wireless communication unit 31. The camera unit 33 is connected to the image synchronization unit 34.

The external apparatus 4D comprises an external controller 46D instead of the external controller 46C and comprise an external apparatus-side processor 48D instead of the external apparatus-side processor 48C, compared to the external apparatus 4C in Embodiment 3.

The image processing unit 81 of the ultrasound probe 2D raster-converts the signal subjected to the envelope detection processing by the signal processing unit 23 into an image signal conforming to a normal television signal scanning system and executes various kinds of necessary image processing, such as brightness correction, gradation correction, sharpness correction, an image size correction, refresh rate correction, scanning frequency correction, and color correction, on the converted image signal, thereby generating an ultrasound image U conforming to a display format for the terminal monitor 36 of the mobile information terminal 3D and an ultrasound image U conforming to a display format for the external monitor 45 of the external apparatus 4D. The image processing unit 81 sends the generated ultrasound images U to the probe-side wireless communication unit 24.

The probe-side wireless communication unit 24 wirelessly transmits the ultrasound image U sent from the image processing unit 81 to the mobile information terminal 3D.

The terminal-side wireless communication unit 31 receives the ultrasound image U wirelessly transmitted from the ultrasound probe 2D and sends the received ultrasound image U to the image synchronization unit 34.

The camera unit 33 acquires a view image C obtained by imaging a scanning point of the ultrasound probe 2D in the subject and sends the acquired view image C to the image synchronization unit 34.

The image synchronization unit 34 synchronizes the ultrasound image U sent from the terminal-side wireless communication unit 31 and the view image C sent from the camera unit 33 with each other and generates a composite image M based on the ultrasound image U and the view image C synchronized with each other. Specifically, the image synchronization unit 34 synchronizes the ultrasound image U conforming to the display format for the terminal monitor 36 of the mobile information terminal 3D and the view image C with each other, and synchronizes the ultrasound image U conforming to the display format for the external monitor 45 of the external apparatus 4D and the view image C with each other.

The image synchronization unit 34 sends the composite image M generated based on the ultrasound image U conforming to the display format for the terminal monitor 36 and the view image C synchronized with each other to the display controller 35.

The display controller 35 executes predetermined processing on the composite image M sent from the image synchronization unit 34, then, sends the composite image M to the terminal monitor 36, and displays the ultrasound image U and the view image C synchronized with each other together on the terminal monitor 36 as shown in FIG. 3.

The image synchronization unit 34 sends the composite image M generated based on the ultrasound image U conforming to the display format for the external monitor 45 and the view image C synchronized with each other to the terminal-side wireless communication unit 31.

The terminal-side wireless communication unit 31 wirelessly transmits the composite image M sent from the image synchronization unit 34 to the external apparatus 4D.

The external wireless communication unit 41 of the external apparatus 4D receives the composite image M wirelessly transmitted from the mobile information terminal 3D and sends the received composite image M to the display controller 44.

The display controller 44 executes predetermined processing on the composite image M sent from the external wireless communication unit 41, then, sends the composite image M to the external monitor 45, and displays the ultrasound image U and the view image C synchronized with each other together on the external monitor 45 as shown in FIG. 4.

From the above description, with the ultrasound system 1D according to Embodiment 4, even in a case where only the ultrasound probe 2D comprises the image processing unit 81 and only the mobile information terminal 3D comprises the image synchronization unit 34, similarly to the ultrasound system 1C of Embodiment 3 in which the mobile information terminal 3C comprises the image processing unit 32 and the external apparatus 4C comprises image processing unit 42, the same view image C and ultrasound image U are displayed on the terminal monitor 36 and the external monitor 45 substantially simultaneously. For this reason, since the observer who observes the view image C and the ultrasound image U with the external apparatus 4D disposed at a remote location can give advice to the operator of the ultrasound probe 2D and the mobile information terminal 3D, an appropriate ultrasound image U is obtained, and it is possible to improve accuracy of ultrasound diagnosis.

In the ultrasound system 1D according to Embodiment 4 of the present invention, similarly to the ultrasound system 1 of Embodiment 1, as the observer who observes the ultrasound image U and the view image C displayed on the external monitor 45 inputs the probe freeze instruction through the input device 47 of the external apparatus 4D, the transmission of the ultrasonic wave from the transducer array 21 of the ultrasound probe 2 is stopped and the imaging of the view image C by the camera unit 33 of the mobile information terminal 3D is stopped, such that the display of the ultrasound image U and the view image C is temporarily stopped in the terminal monitor 36 of the mobile information terminal 3D and the external monitor 45 of the external apparatus 4D simultaneously.

For this reason, for example, even in a case where the level of skill of the operator of the ultrasound probe 2 and the mobile information terminal 3D is low and hardly determines whether or not an appropriate ultrasound image U is obtained, the observer having a high level of skill inputs the probe freeze instruction through the input device 47 of the external apparatus 4D, whereby the display of the ultrasound image U is temporarily stopped at an appropriate timing in the terminal monitor 36 and the external monitor 45. Accordingly, it is possible to obtain an appropriate ultrasound image U. With this, it is possible to improve accuracy of ultrasound diagnosis.

Embodiment 5

Figure 14:
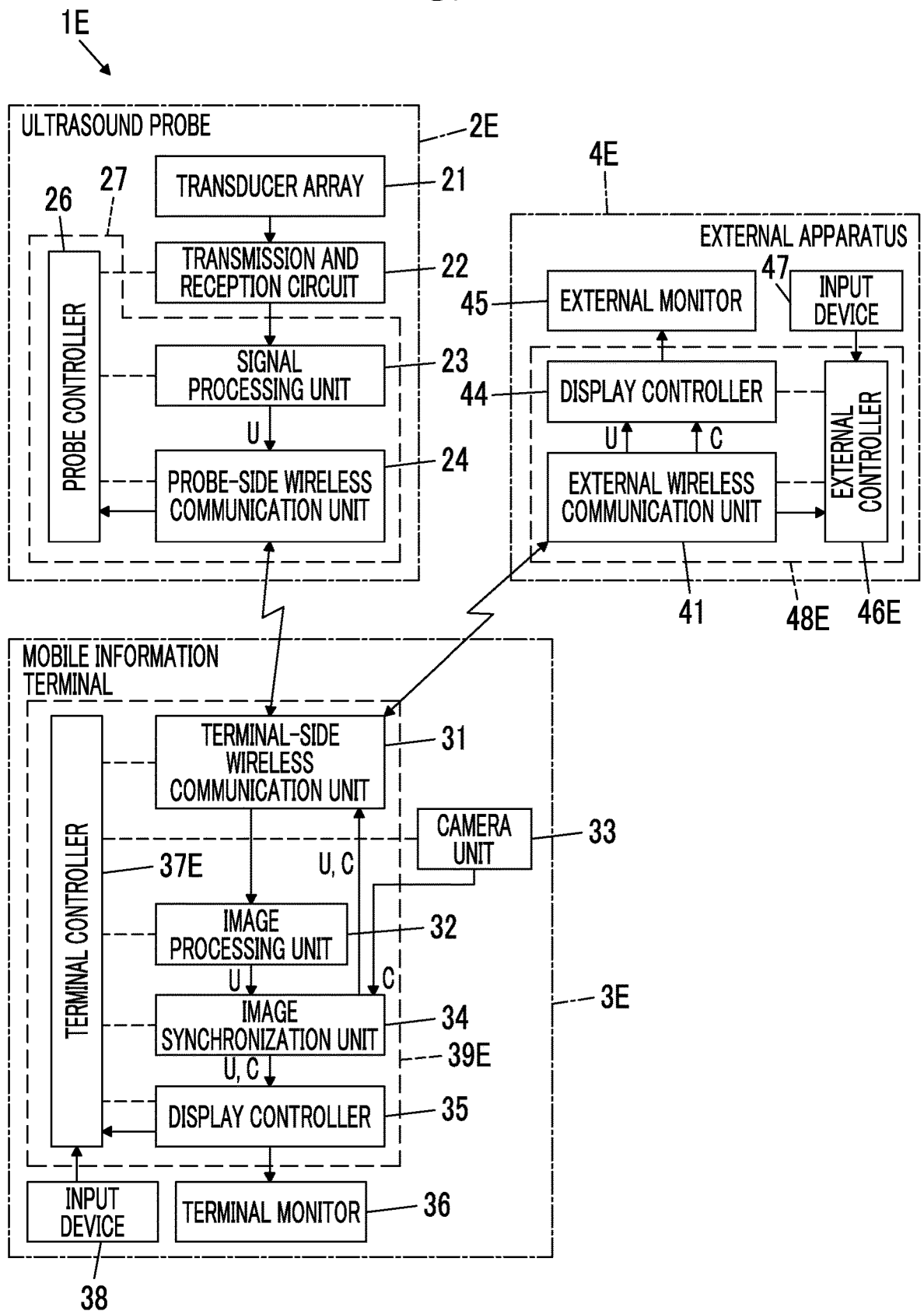
FIG. 14 is a block diagram showing the configuration of an ultrasound system according to Embodiment 5 of the present invention.

In Embodiment 3, since the external apparatus 4C receives the composite image M from the mobile information terminal 3C and displays the received composite image M on the external monitor 45, the disposition and the size of the ultrasound image U and the view image C displayed on the external monitor 45 can be freely changed on the external apparatus 4C side; however, with an ultrasound system 1E of Embodiment 5 shown in FIG. 14, the disposition and the size of the ultrasound image U and the view image C displayed on the external monitor 45 can be arbitrarily changed on an external apparatus 4E side.

FIG. 14 shows the configuration of an ultrasound system 1E according to Embodiment 5 of the present invention. The ultrasound system 1E comprises an ultrasound probe 2E having the same internal configuration as the ultrasound probe 2C, comprises a mobile information terminal 3E instead of the mobile information terminal 3C, and comprises an external apparatus 4E instead of the external apparatus 4C, compared to the ultrasound system 1C of Embodiment 3. The ultrasound probe 2E is connected only to the mobile information terminal 3E by wireless communication, and the external apparatus 4E is connected only to the mobile information terminal 3E by wireless communication.

The mobile information terminal 3E comprises a terminal controller 37E instead of the terminal controller 37 and comprises a terminal-side processor 39E instead of the terminal-side processor 39, compared to the mobile information terminal 3C in Embodiment 3. In the mobile information terminal 3E, the image synchronization unit 34 is connected to the camera unit 33, and the image synchronization unit 34 is connected to the terminal-side wireless communication unit 31.

The external apparatus 4E comprises an external controller 46E instead of the external controller 46 and comprises an external apparatus-side processor 48E instead of the external apparatus-side processor 48, compared to the external apparatus 4C in Embodiment 3.

The probe-side wireless communication unit 24 of the ultrasound probe 2E wirelessly transmits the reception data before imaging subjected to the envelope detection processing by the signal processing unit 23 to the mobile information terminal 3E.

The terminal-side wireless communication unit 31 of the mobile information terminal 3E receives the reception data before imaging wirelessly transmitted from the ultrasound probe 2E and sends the received reception data before imaging to the image processing unit 32.

The image processing unit 32 generates an ultrasound image U conforming to a display format for the terminal monitor 36 of the mobile information terminal 3E and an ultrasound image U conforming to a display format for the external monitor 45 of the external apparatus 4E based on the reception data before imaging sent from the terminal-side wireless communication unit 31. The image processing unit 32 sends the ultrasound images U to the image synchronization unit 34.

The camera unit 33 acquires a view image C obtained by imaging a scanning point of the ultrasound probe 2E in the subject and sends the acquired view image C to the image synchronization unit 34.

The image synchronization unit 34 synchronizes the ultrasound image U sent from the terminal-side wireless communication unit 31 and the view image C sent from the camera unit 33 with each other. Specifically, the image synchronization unit 34 synchronizes the ultrasound image U conforming to the display format for the terminal monitor 36 of the mobile information terminal 3E and the view image C with each other, and synchronizes the ultrasound image U conforming to the display format for the external monitor 45 of the external apparatus 4E and the view image C with each other.

The image synchronization unit 34 sends each of the ultrasound image U and the view image C to the display controller 35, instead of generating one composite image M based on the ultrasound image U conforming to the display format for the terminal monitor 36 and the view image C synchronized with each other.

The display controller 35 executes predetermined processing on the ultrasound image U and the view image C sent from the image synchronization unit 34 and displays the ultrasound image U and the view image C synchronized with each other together on the terminal monitor 36 as shown in FIG. 3.

The image synchronization unit 34 sends each of the ultrasound image U and the view image C to the terminal-side wireless communication unit 31, instead of generating one composite image M based on the ultrasound image U conforming to the display format for the external monitor 45 and the view image C synchronized with each other.

The terminal-side wireless communication unit 31 wirelessly transmits the ultrasound image U and the view image C sent from the image synchronization unit 34 to the external apparatus 4E.

The external wireless communication unit 41 of the external apparatus 4E receives the ultrasound image U and the view image C wirelessly transmitted from the mobile information terminal 3E and sends each of the received ultrasound image U and view image C to the display controller 44.

The display controller 44 executes predetermined processing on the ultrasound image U and the view image C sent from the external wireless communication unit 41 and displays the ultrasound image U and the view image C synchronized with each other together on the external monitor 45.

Figure 15:
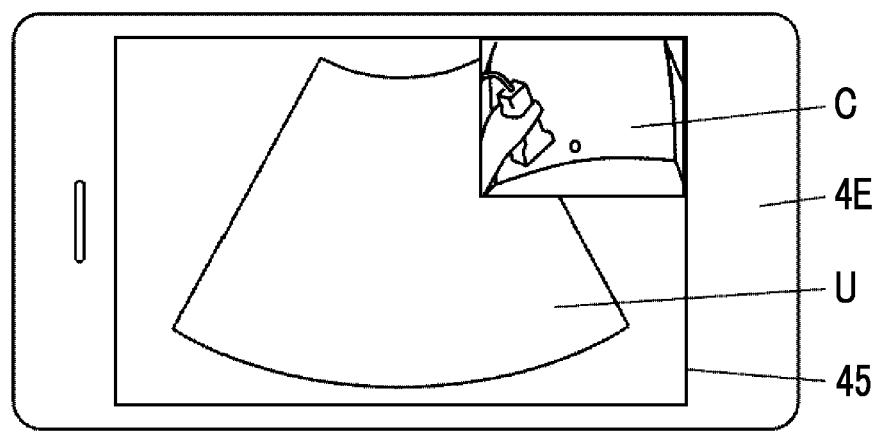
FIG. 15 is a diagram schematically showing an example of an ultrasound image and a view image that are displayed on an external apparatus in Embodiment 5 of the present invention.

Here, the disposition and the size including display positions and size of the ultrasound image U and the view image C displayed on the external monitor 45 can be adjusted by an input operation of the observer through the input device 47. For example, in a case where the observer inputs instruction information for the guidance on adjusting the disposition and the size of the ultrasound image U and the view image C on the external monitor 45 through the input device 47, the input instruction information is input to the display controller 44 by way of the external controller 46E. The display controller 44 displays the ultrasound image U and the view image C synchronized with each other, for example, with the disposition and the size as shown in FIG. 15 based on the input instruction information. In an example shown in FIG. 15, the external apparatus 4E, the ultrasound image U, and the view image C are rotated at 90 degrees, and the ultrasound image U and the view image C are displayed on the external monitor 45 such that the view image C is superimposed on a part of the ultrasound image U, compared to the example shown in FIG. 4.

From the above description, with the ultrasound system 1E according to Embodiment 5 of the present invention, the disposition and the size of the ultrasound image U and the view image C displayed on the external monitor 45 of the external apparatus 4E can be adjusted. Thus, the observer who observes the ultrasound image U and the view image C displayed on the external monitor 45 can more clearly confirm the ultrasound image U and the view image C conforming to the observer's preference.

Embodiment 6

In Embodiment 5, although the reception data before imaging subjected to the envelope detection processing by the signal processing unit 23 is wirelessly transmitted to the mobile information terminal 3E by the probe-side wireless communication unit 24, the ultrasound image U may be generated in the ultrasound probe 2.

Figure 16:
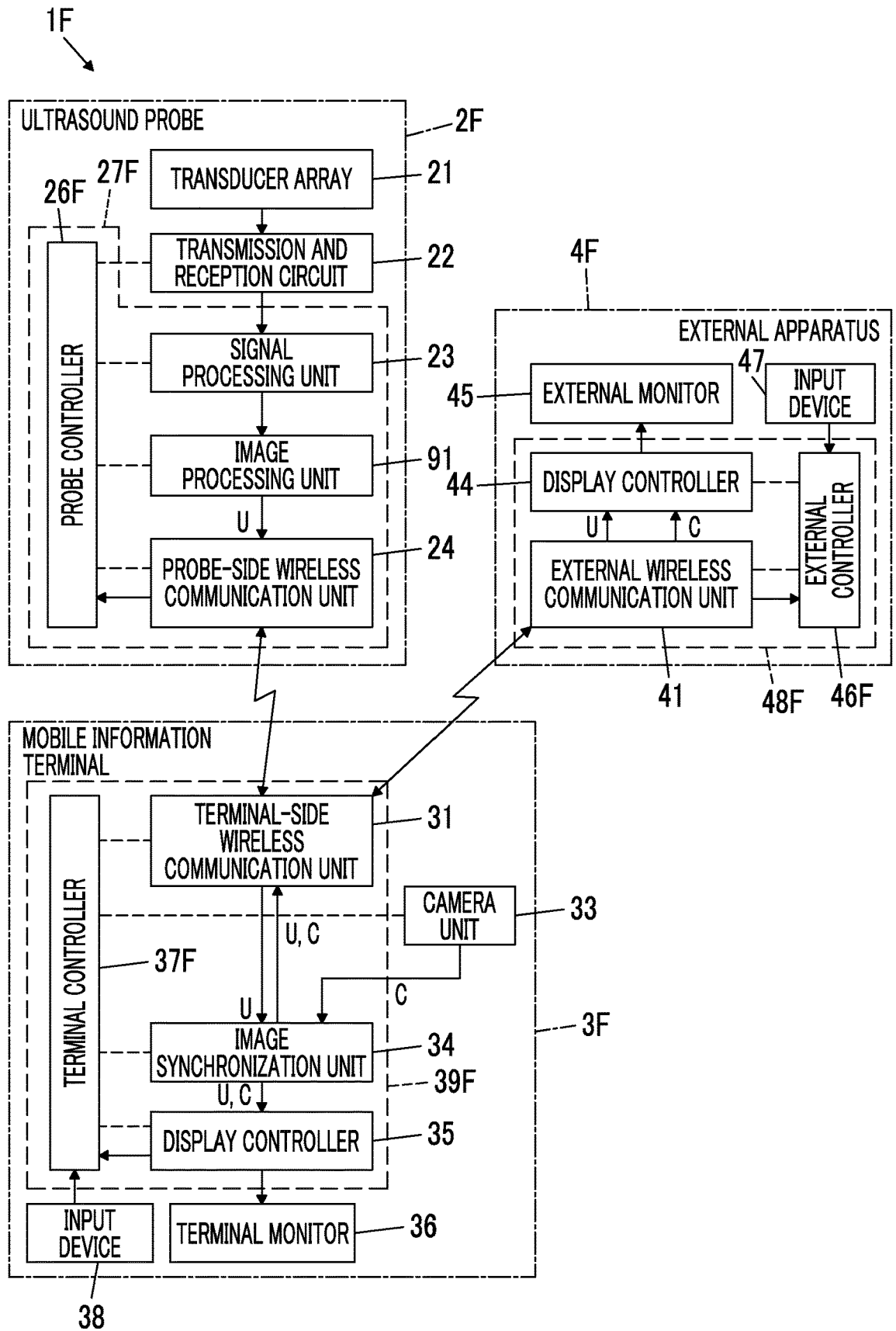
FIG. 16 is a block diagram showing the configuration of an ultrasound system according to Embodiment 6 of the present invention.

FIG. 16 shows the configuration of an ultrasound system 1F according to Embodiment 6 of the present invention. The ultrasound system 1F comprises an ultrasound probe 2F instead of the ultrasound probe 2E, comprises a mobile information terminal 3F instead of the mobile information terminal 3E, and comprises an external apparatus 4F instead of the external apparatus 4E, compared to the ultrasound system 1E of Embodiment 5 shown in FIG. 14. The ultrasound probe 2F is connected only to the mobile information terminal 3F by wireless communication, and the external apparatus 4F is connected only to the mobile information terminal 3F by wireless communication.

The ultrasound probe 2F is further provided with an image processing unit 91, comprises a probe controller 26F instead of the probe controller 26, and comprises a probe-side processor 27F instead of the probe-side processor 27, compared to the ultrasound probe 2E in Embodiment 5. In the ultrasound probe 2F, the image processing unit 91 is connected to the signal processing unit 23, and the probe-side wireless communication unit 24 and the probe controller 26F are connected to the image processing unit 91. Though not shown, the signal processing unit 23 and the image processing unit 91 configure an ultrasound image generation unit.

The mobile information terminal 3F is not provided with the image processing unit 32, comprises a terminal controller 37F instead of the terminal controller 37E, and comprises a terminal-side processor 39F instead of the terminal-side processor 39E, compared to the mobile information terminal 3E in Embodiment 5. In the mobile information terminal 3F, the image synchronization unit 34 is connected to the terminal-side wireless communication unit 31. The camera unit 33 is connected to the image synchronization unit 34.

The external apparatus 4F comprises an external controller 46F instead of the external controller 46E and comprises an external apparatus-side processor 48F instead of the external apparatus-side processor 48E, compared to the external apparatus 4E in Embodiment 5.

The image processing unit 91 of the ultrasound probe 2F raster-converts the signal subjected to the envelope detection processing by the signal processing unit 23 into an image signal conforming to a normal television signal scanning system and executes various kinds of necessary image processing, such as brightness correction, gradation correction, sharpness correction, an image size correction, refresh rate correction, scanning frequency correction, and color correction, on the converted image signal, thereby generating an ultrasound image U conforming to the display format for the terminal monitor 36 of the mobile information terminal 3F and an ultrasound image U conforming to a display format for the external monitor 45 of the external apparatus 4F. The image processing unit 91 sends the generated ultrasound images U to the probe-side wireless communication unit 24.

The terminal-side wireless communication unit 31 receives the wirelessly ultrasound image U transmitted from the ultrasound probe 2F and sends the received ultrasound image U to the image synchronization unit 34.

The camera unit 33 acquires a view image C obtained by a scanning point of the ultrasound probe 2F in the subject and sends the acquired view image C to the image synchronization unit 34.

The image synchronization unit 34 synchronizes the ultrasound image U sent from the terminal-side wireless communication unit 31 and the view image C sent from the camera unit 33 with each other. Specifically, the image synchronization unit 34 synchronizes the ultrasound image U conforming to the display format for the terminal monitor 36 of the mobile information terminal 3F and the view image C with each other, and synchronizes the ultrasound image U conforming to the display format for the external monitor 45 of the external apparatus 4F and the view image C with each other.

The image synchronization unit 34 sends each of the ultrasound image U and the view image C to the display controller 35, instead of generating one composite image M based on the ultrasound image U conforming to the display format for the terminal monitor 36 and the view image C synchronized with each other.

The display controller 35 executes predetermined processing on the ultrasound image U and the view image C sent from the image synchronization unit 34 and displays the ultrasound image U and the view image C synchronized with each other together on the terminal monitor 36.

The image synchronization unit 34 sends each of the ultrasound image U and the view image C to the terminal-side wireless communication unit 31, instead of generating one composite image M based on the ultrasound image U conforming to the display format for the external monitor 45 and the view image C synchronized with each other.

The terminal-side wireless communication unit 31 wirelessly transmits the ultrasound image U and the view image C sent from the image synchronization unit 34 to the external apparatus 4F.

The external wireless communication unit 41 of the external apparatus 4F receives the ultrasound image U and the view image C wirelessly transmitted from the mobile information terminal 3F and sends each of the received ultrasound image U and view image C to the display controller 44.

The display controller 44 executes predetermined processing on the ultrasound image U and the view image C sent from the external wireless communication unit 41 and displays the ultrasound image U and the view image C synchronized with each other together on the external monitor 45.

In this case, the display controller 44 can adjust the disposition and the size of the ultrasound image U and the view image C displayed on the external monitor 45 in response to an input operation of the observer through the input device 47. With this, for example, as shown in FIG. 15, the ultrasound image U and the view image C synchronized with each other are displayed together on the external monitor 45.

From the above description, with the ultrasound system 1F according to Embodiment 6 of the present invention, even in a case where the ultrasound probe 2F comprises the image processing unit 91, the disposition and the size of the ultrasound image U and the view image C displayed on the external monitor 45 of the external apparatus 4F can be adjusted. Thus, the observer who observes the ultrasound image U and the view image C displayed on the external monitor 45 can more clearly confirm the ultrasound image U and the view image C conforming to the observer's preference.

Embodiment 7

In Embodiment 1, the ultrasound image U and the view image C captured by the operator of the ultrasound probe 2 and the mobile information terminal 3 are displayed in the external monitor 45 of the external apparatus 4 in real time, the ultrasound image U and the view image C captured during inspection may be stored, and the stored ultrasound image U and view image C may be displayed as a so-called thumbnail image on the external monitor 45.

Figure 17:
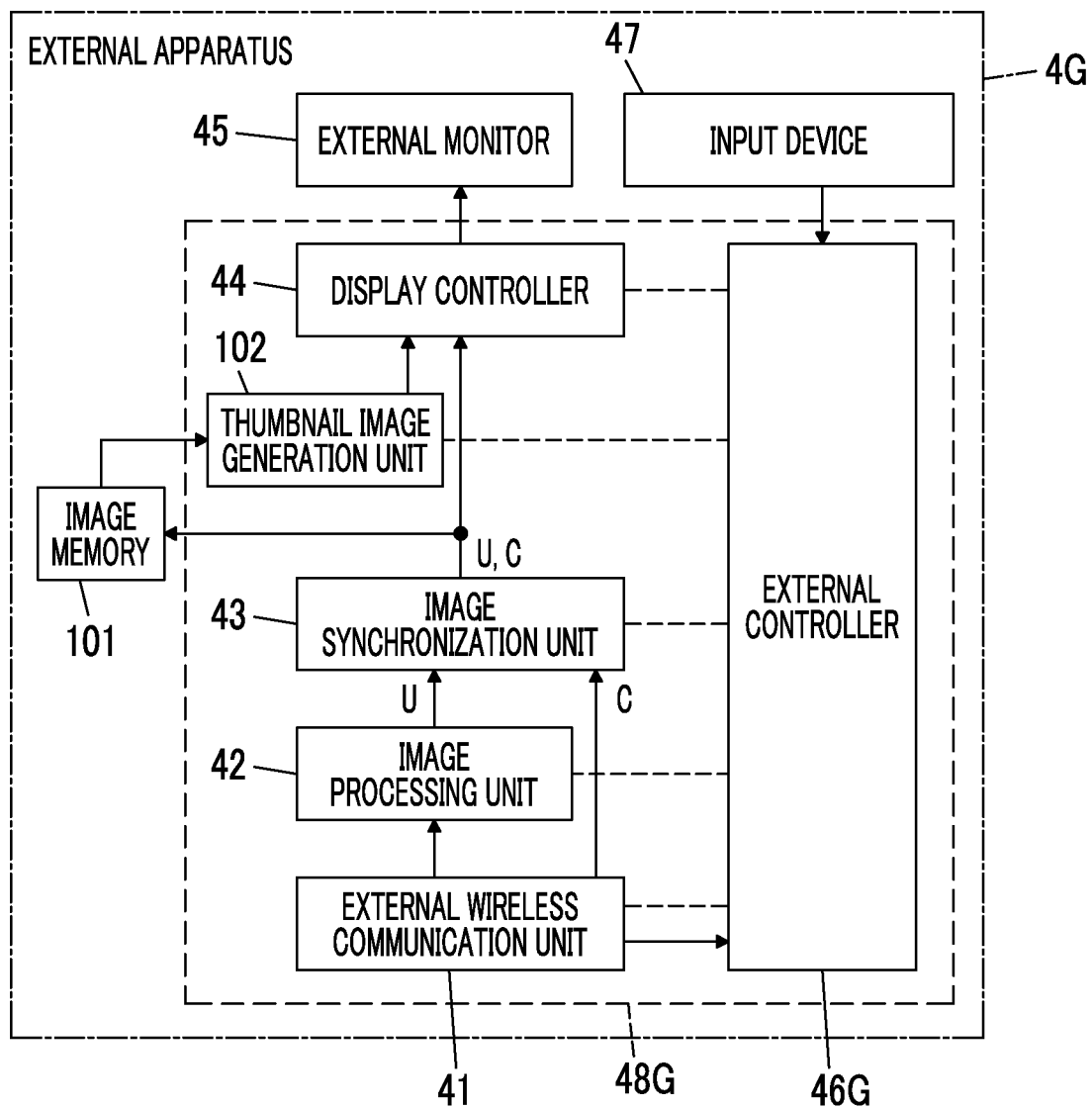
FIG. 17 is a block diagram showing the configuration of an external apparatus in Embodiment 7 of the present invention.

FIG. 17 shows the configuration of an external apparatus 4G in Embodiment 7 of the present invention. An ultrasound system according to Embodiment 7 comprises an external apparatus 4G shown in FIG. 17 instead of the external apparatus 4, compared to the ultrasound system 1 of Embodiment 1 shown in FIG. 1, and the ultrasound probe 2, the mobile information terminal 3, and the external apparatus 4G are connected to one another by wireless communication.

As shown in FIG. 17, the external apparatus 4G is further provided with an image memory 101 and a thumbnail image generation unit 102, comprises an external controller 46G instead of the external controller 46, and an external apparatus-side processor 48G instead of the external apparatus-side processor 48, compared to the external apparatus 4 in Embodiment 1. In the external apparatus 4G, the image memory 101 is connected to the image synchronization unit 43, and the thumbnail image generation unit 102 is connected to the image memory 101. The display controller 44 and the external controller 46G are connected to the thumbnail image generation unit 102.

The image memory 101 is a memory that stores the ultrasound image U and the view image synchronized with each other by the image synchronization unit 43. As the image memory 101, for example, a flash memory, a RAM, an SD card, or an SSD can be used.

For example, in a state in which the transmission of the ultrasonic wave from the transducer array 21 of the ultrasound probe 2 and the imaging of the view image C by the camera unit 33 of the mobile information terminal 3 are stopped, and the display of the ultrasound image U and the view image C is temporarily stopped in the terminal monitor 36 of the mobile information terminal 3 and the external monitor 45 of the external apparatus 4G, with an input of an instruction for the guidance on storing the ultrasound image U and the view image C through the input device 47 of the external apparatus 4G or the input device 38 of the mobile information terminal 3 as a trigger, the ultrasound image U and the view image C synchronized with each other by the image synchronization unit 43 can be stored in the image memory 101.

More specifically, for example, as shown in FIGS. 3 and 4, in a state in which the display of the ultrasound image U and the view image C is temporarily stopped in the terminal monitor 36 and the external monitor 45 with the touch on the freeze button B1 displayed on the terminal monitor 36 or the freeze button B1 displayed on the external monitor 45, as the store button B2 displayed on the terminal monitor 36 or the store button B2 displayed on the external monitor 45 is further touched, the ultrasound image U and the view image C displayed in the temporarily stopped state in each of the terminal monitor 36 and the external monitor 45 can be stored in the image memory 101.

Figure 18:
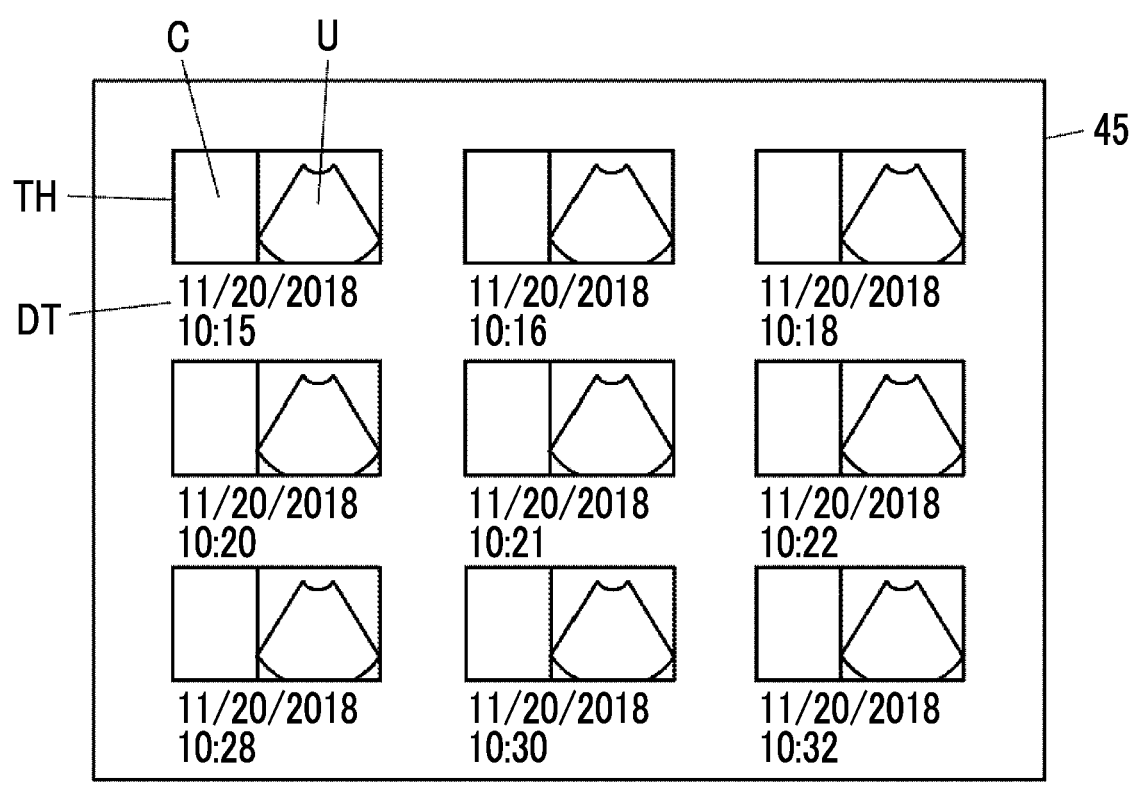
FIG. 18 is a schematic view showing an example of thumbnail images that are displayed on an external monitor in Embodiment 7 of the present invention.

As shown in FIG. 18, the thumbnail image generation unit 102 generates thumbnail images TH each consisting of the ultrasound image U and the view image C stored in the image memory 101 and displays the generated thumbnail image TH on the external monitor 45. For example, as instruction information for the guidance on displaying the thumbnail image TH on the external monitor 45 is input from the observer through the input device 47 of the external apparatus 4G, the thumbnail image TH is displayed on the external monitor 45. In an example of FIG. 18, a plurality of thumbnail images TH each consisting of the ultrasound image U and the view image C synchronized with each other are displayed in a list on the external monitor 45, and date and time DT on which the ultrasound image U and the view image C synchronized with each other are captured is displayed close to each thumbnail image TH.

From the above description, with the ultrasound system according to Embodiment 7 of the present invention, each time the probe freeze instruction is input from the input device 47 of the external apparatus 4G and the input device 38 of the mobile information terminal 3, the ultrasound image U and the view image C synchronized with each other by the image synchronization unit 43 are stored in the image memory 101, the thumbnail image TH is generated based on the ultrasound image U and the view image C stored in the image memory 101 by the thumbnail image generation unit 102, and the generated thumbnail image TH is displayed on the external monitor 45. Therefore, for example, the observer who views the external monitor 45 can compare and examine a plurality of ultrasound images U and view images C captured during inspection by confirming a plurality of thumbnail images TH displayed in a list on the external monitor 45 and can give more appropriate advice to the operator of the ultrasound probe 2 and the mobile information terminal 3. With this, it is possible to improve accuracy of ultrasound diagnosis.

Although an example where the ultrasound image U and the view image C synchronized with each other by the image synchronization unit 43 are stored in the image memory 101 has been described, for example, instead of each of the ultrasound image U and the view image C being stored in the image memory 101, the composite image M generated based on the ultrasound image U and the view image C synchronized with each other may be stored in the image memory 101.

Although the image memory 101 is included in the external apparatus 4G, for example, the mobile information terminal 3 may include the image memory 101 instead of the external apparatus 4G including in the image memory 101, or each of both the external apparatus 4G and the mobile information terminal 3 may include the image memory 101. In a case where the mobile information terminal 3 includes the image memory 101 instead of the external apparatus 4G including the image memory 101, for example, the ultrasound image U and the view image C stored in the image memory 101 can be wirelessly transmitted from the terminal-side wireless communication unit 31 of the mobile information terminal 3 to the external wireless communication unit 41 of the external apparatus 4G, and can be further sent from the external wireless communication unit 41 to the thumbnail image generation unit 102.

In a case where one of a plurality of thumbnail images TH displayed on the external monitor 45 may be selected by the observer who views the external monitor 45, through the input device 47 of the external apparatus 4G, as shown in FIGS. 3 and 4, the ultrasound image U and the view image C corresponding to the selected thumbnail image TH may be displayed on the external monitor 45 and the terminal monitor 36 of the mobile information terminal 3. With this, since the observer who views the external monitor 45 can give an instruction for reimaging of the ultrasound image U, advice, or the like to the operator of the ultrasound probe 2 and the mobile information terminal 3 while confirming specific ultrasound image U and view image C, it is possible to improve accuracy of ultrasound diagnosis.

In Embodiment 7, each time the probe freeze instruction is input through the input device 47 of the external apparatus 4G and the input device 38 of the mobile information terminal 3, and instruction information for the guidance on storing the ultrasound image U and the view image C is input, the ultrasound image U and the view image C are stored in the image memory 101. In contrast, for example, a configuration may be made in which the ultrasound image U and the view image C are automatically stored in the image memory 101 merely as the probe freeze instruction is input through the input device 47 of the external apparatus 4G and the input device 38 of the mobile information terminal 3, without inputting the instruction information for the guidance on storing the ultrasound image U and the view image C. With this, steps that are performed by the observer who observes the ultrasound image U and the view image C displayed on the external monitor 45 and the operator of the ultrasound probe 2 and the mobile information terminal 3, to store the ultrasound image U and the view image C can be reduced, and the ultrasound image U and the view image C can be more easily stored in the image memory 101.

For example, though not shown, as the ultrasound image U and the view image C corresponding to the thumbnail image TH are stored in the image memory 101, the instruction information transmission source information representing through which of the input device 38 of the mobile information terminal 3 and the input device 47 of the external apparatus 4 the probe freeze instruction is input, can be displayed on the external monitor 45 corresponding to each thumbnail image TH. For example, as the instruction information transmission source information, a message "remote freeze", "local freeze", or the like may be displayed close to the thumbnail image TH, two kinds of icons that are different in shape, size, color, or the like may be displayed close to the thumbnail image TH, or two kinds of frame lines that are different in shape, size, thickness, color, or the like may be displayed to surround the thumbnail image TH. With this, the observer who observes the external monitor 45 can easily recognize the ultrasound image U and the view image C stored with the input of the probe freeze instruction through either the input device 38 of the mobile information terminal 3 or the input device 47 of the external apparatus 4 to which the thumbnail image TH displayed on the external monitor 45 corresponds and can refer to the ultrasound image U and the view image C in comparing and examining a plurality of thumbnail images TH.

Although the aspect of Embodiment 7 has shown the application to Embodiment 1, Embodiment 7 can be similarly applied to Embodiment 2 to Embodiment 6.

Embodiment 8

In Embodiment 1, as the probe freeze instruction is input through the input device 38 of the mobile information terminal 3 or the input device 47 of the external apparatus 4, the ultrasound image U and the view image C synchronized with each other are displayed in the temporarily stopped state in the terminal monitor 36 of the mobile information terminal 3 and the external monitor 45 of the external apparatus 4. In contrast, measurement on a measurement target in the ultrasound image U displayed in a temporarily stopped state may be performed with an input operation through the input device 47 of the external apparatus 4. Here, the measurement target indicates a target of measurement, such as a part of the subject included in the ultrasound image U.

Figure 19:
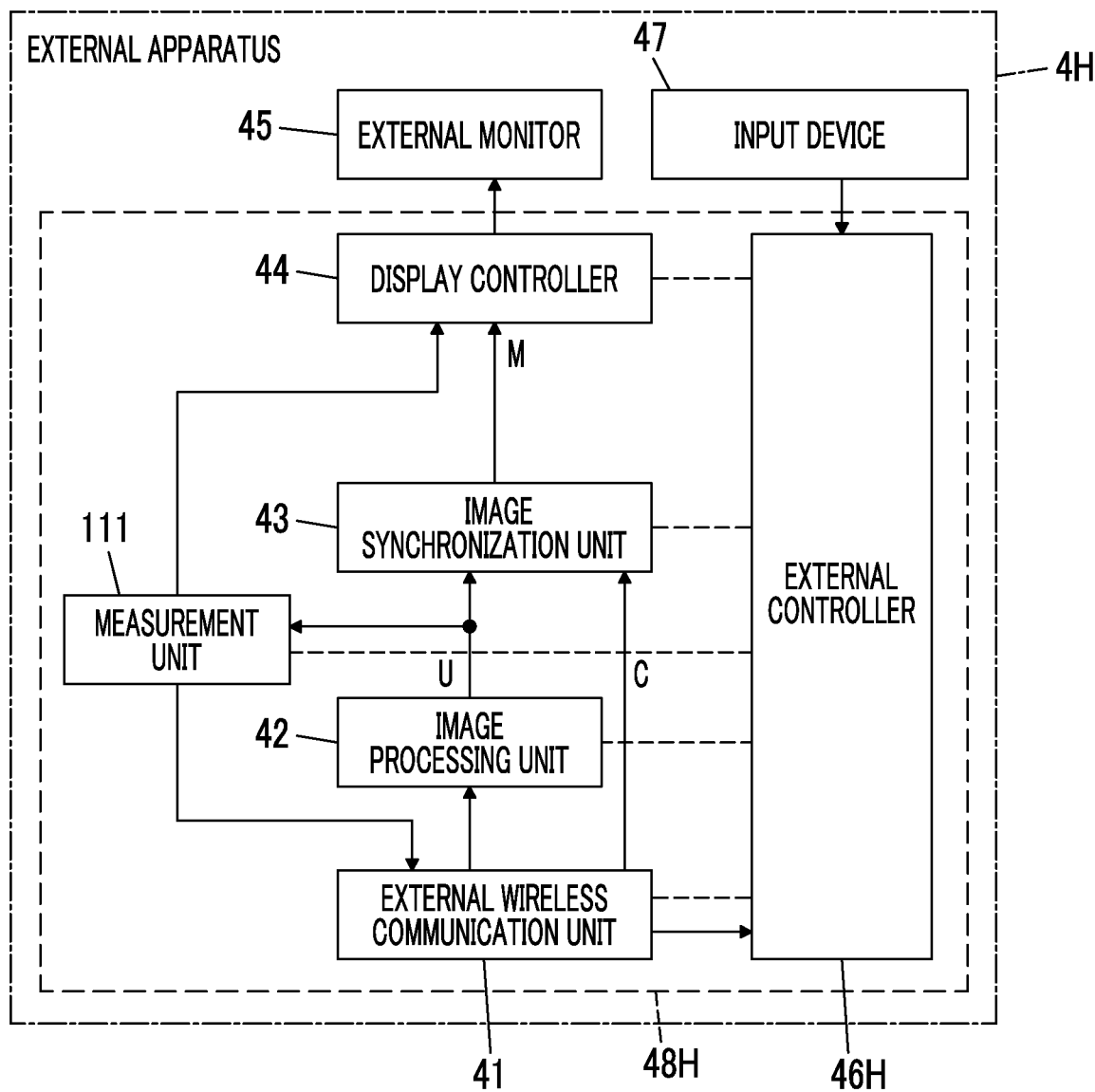
FIG. 19 is a block diagram showing the configuration of an external apparatus in Embodiment 8 of the present invention.

FIG. 19 shows an external apparatus 4H in Embodiment 8 of the present invention. An ultrasound system according to Embodiment 8 comprises an external apparatus 4H shown in FIG. 19 instead of the external apparatus 4, compared to the ultrasound system 1 of Embodiment 1 shown in FIG. 1, and the ultrasound probe 2, the mobile information terminal 3, and the external apparatus 4H are connected to one another by wireless communication.

As shown in FIG. 19, the external apparatus 4H is further provided with a measurement unit 111, comprises an external controller 46H instead of the external controller 46, and an external apparatus-side processor 48H instead of the external apparatus-side processor 48, compared to the external apparatus 4 in Embodiment 1. In the external apparatus 4H, the measurement unit 111 is connected to the image processing unit 42. The external wireless communication unit 41, the display controller 44, and the external controller 46H are connected to the measurement unit 111.

The measurement unit 111 analyzes the ultrasound image U generated by the image processing unit 42 to perform measurement on a measurement target in the ultrasound image U. For example, as an instruction for the guidance on performing measurement is input from the observer through the input device 47 of the external apparatus 4H, the ultrasound image U for use in the measurement is displayed on the external monitor 45. The measurement unit 111 can perform measurement, such as measuring a distance between two points in the displayed ultrasound image U, based on an input operation of the observer through the input device 47. A process in which the measurement is performed in this manner and a measurement result can be displayed on the external monitor 45, but can also be displayed on the terminal monitor 36 of the mobile information terminal 3 simultaneously.

From the above description, with the ultrasound system according to Embodiment 8 of the present invention, since the measurement on the measurement target in the ultrasound image U by the measurement unit 111 conforming to the input operation through the input device 47 of the external apparatus 4H, the observer who observes the external monitor 45 can obtain more detailed information on the captured ultrasound image U. Therefore, the observer can give more appropriate advice to the operator of the ultrasound probe 2 and the mobile information terminal 3 based on the obtained information, for example.

In Embodiment 8, the external apparatus 4H includes the measurement unit 111, and the measurement on the measurement target in the ultrasound image U is performed conforming to the input operation of the observer through the input device 47 of the external apparatus 4H. In contrast, for example, the mobile information terminal 3 may comprise the measurement unit 111, and the measurement on the measurement target in the ultrasound image U is performed conforming to an input operation of the operator through the input device 38 of the mobile information terminal 3. In this case, a process and a result of the measurement in the mobile information terminal 3 can be displayed on the external monitor 45 of the external apparatus 4H. With this, for example, the observer who observes the external monitor 45 can give advice to the operator about the measurement that is performed by the operator of the ultrasound probe 2 and the mobile information terminal 3.

Figure 20:
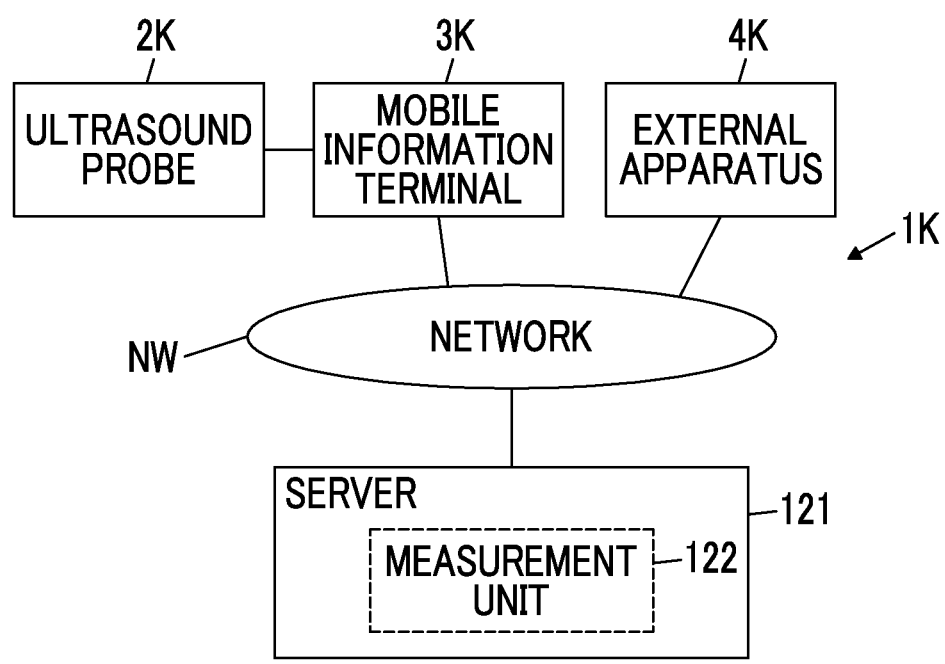
FIG. 20 is a block diagram showing the configuration of an ultrasound system according to a modification example of Embodiment 8 of the present invention.

For example, a server that is connected to the mobile information terminal 3 and the external apparatus 4H by a network may comprise the measurement unit 111. FIG. 20 shows the configuration of an ultrasound system 1K according to a modification example of Embodiment 8 of the present invention. In the ultrasound system 1K, the ultrasound probe 2K is connected to a mobile information terminal 3K, and the mobile information terminal 3K and an external apparatus 4K are connected to a server 121 through a network NW. The server 121 comprises a measurement unit 122. The ultrasound probe 2K, the mobile information terminal 3K, and the external apparatus 4K are the same as the ultrasound probe 2, the mobile information terminal 3, and the external apparatus 4 in Embodiment 1, respectively.

For example, in a state in which the transmission of the ultrasonic wave from the transducer array 21 and the imaging of the view image C by the camera unit 33 are stopped and the display of the ultrasound image U and the view image C is temporarily stopped in the terminal monitor 36 and the external monitor 45, with an input of an instruction for the guidance on performing measurement from the observer through the input device 47 of the external apparatus 4K as a trigger, the measurement unit 122 of the server 121 can perform the measurement on the measurement target in the ultrasound image U conforming to the measurement instruction of the observer input through the input device 47 on the ultrasound image U displayed on the external monitor 45.

For example, in a state in which the transmission of the ultrasonic wave from the transducer array 21 and the imaging of the view image C by the camera unit 33 are stopped and the display of the ultrasound image U and the view image C is temporarily stopped in the terminal monitor 36 and the external monitor 45, with an input of an instruction for the guidance on performing measurement from the operator through the input device 38 of the mobile information terminal 3 as a trigger, the measurement unit 122 of the server 121 may perform the measurement on the measurement target in the ultrasound image U.

In this way, in a case where the server 121 that is connected to the mobile information terminal 3K and the external apparatus 4K through the network NW includes the measurement unit 122, as the server 121 is configured with a computer having high calculation ability, it is possible to execute advanced calculation or the like using artificial intelligence (AI), for example. For this reason, with the measurement unit 122 of the server 121, for example, a bladder of the subject is included in the ultrasound image U, and complicated calculation for calculating a urine volume in the bladder by calculating the volume of the bladder can be easily executed. Therefore, the observer who observes the external monitor 45 can obtain more detailed information on the captured ultrasound image U and can give more appropriate advice to the operator of the ultrasound probe 2K and the mobile information terminal 3K.

Although the aspect of Embodiment 8 has shown the application to Embodiment 1, Embodiment 8 can be similarly applied to Embodiment 2 to Embodiment 7.

EXPLANATION OF REFERENCES 1, 1B, 1C, 1D, 1E, 1F, 1K: ultrasound system
2, 2B, 2C, 2D, 2E, 2F, 2K: ultrasound probe
3, 3A, 3B, 3C, 3D, 3E, 3F, 3K: mobile information terminal
4, 4A, 4B, 4C, 4D, 4E, 4F, 4G, 4H, 4K: external apparatus
21: transducer array
22: transmission and reception circuit
23: signal processing unit
24: probe-side wireless communication unit
26, 26B, 26D, 26F: probe controller
27, 27B, 27D, 27F: probe-side processor
31: terminal-side wireless communication unit
32, 42, 71, 81, 91: image processing unit
33: camera unit
34, 43: image synchronization unit
35, 44: display controller
36: terminal monitor
37, 37A, 37B, 37C, 37D, 37E, 37F: terminal controller
38, 47: input device
39, 39A, 39B, 39C, 39D, 39E, 39F: terminal-side processor
41: external wireless communication unit
45: external monitor
46, 46A, 46B, 46C, 46D, 46E, 46F, 46G, 46H: external controller
48, 48A, 48B, 48C, 48D, 48E, 48F, 48G, 48H: external apparatus-side processor
51: pulser
52: amplification unit
53: AD conversion unit
54: beamformer
61, 63: microphone
62, 64: speaker
101: image memory
102: thumbnail image generation unit
111, 122: measurement unit 121: server
A: cursor
B1: freeze button
B2: store button
C: view image
DT: date
H: frame line
K: message
N: stop icon
NW: network
TH: thumbnail image
U: ultrasound image

What is claimed is:

1. An ultrasound system comprising:
an ultrasound probe;
a mobile information terminal; and
an external apparatus,
wherein the ultrasound probe includes
a transducer array,
a transmission and reception circuit configured to transmit an ultrasonic wave from the transducer array and generate a sound ray signal based on a reception signal acquired by the transducer array,
a first processor configured to
generate an ultrasound image based on the sound ray signal generated by the transmission and reception circuit,
give a time stamp representing a time at which the ultrasound image is generated to the ultrasound image, and
wirelessly transmit the ultrasound image,
the mobile information terminal includes
a camera unit configured to
acquire a view image obtained by imaging a scanning point of the ultrasound probe in a subject, and
give a time stamp representing a time at which the view image is generated to the view image, and
a second processor configured to
synchronize the ultrasound image and the view image captured at the same timing with each other by referring to the time stamp given to the ultrasound image wirelessly transmitted from the first processor and the time stamp given to the view image acquired by the camera unit, and
wirelessly transmit the ultrasound image and the view image synchronized with each other,
the external apparatus includes
an external monitor,
a third processor configured to
wirelessly communicate with at least the second processor,
display the ultrasound image and the view image synchronized with each other by the second processor and wirelessly transmitted from the second processor on the external monitor, and
an external input device, and
wherein, when a probe freeze instruction is input from the external input device,
the third processor of the external apparatus is further configured to transmit the probe freeze instruction to the ultrasound probe, and
the first processor of the ultrasound probe is further configured to stop the transmission of the ultrasonic wave from the transducer array by the transmission and reception circuit of the ultrasound probe.

2. The ultrasound system according to claim 1,
wherein, when the probe freeze instruction is input from the external input device, the probe freeze instruction is transmitted from the third processor of the external apparatus to the first processor of the ultrasound probe through the second processor of the mobile information terminal.

3. The ultrasound system according to claim 1,
wherein, when the probe freeze instruction is input from the external input device, the third processor of the external apparatus is configured to transmit the probe freeze instruction to the first processor of the ultrasound probe.

4. The ultrasound system according to claim 1,
wherein the third processor of the external apparatus is further configured to wirelessly communicate with the ultrasound probe and the mobile information terminal, and
the first processor of the ultrasound probe is further configured to wirelessly transmit the ultrasound image to both the mobile information terminal and the external apparatus.

5. The ultrasound system according to claim 1,
wherein the first processor of the ultrasound probe is further configured to wirelessly transmit the ultrasound image to the mobile information terminal, and
the second processor of the mobile information terminal is further configured to wirelessly transmit the ultrasound image wirelessly transmitted from the ultrasound probe and the view image acquired by the camera unit to the external apparatus.

6. The ultrasound system according to claim 1,
wherein the external monitor includes a microphone, and
the first processor of the ultrasound probe is further configured to release the stop of the transmission of the ultrasonic wave from the transducer array based on voice input through the microphone.

7. The ultrasound system according to claim 1,
wherein the third processor of the external apparatus is further configured to analyze the ultrasound image to perform measurement on a measurement target in the ultrasound image.

8. The ultrasound system according to claim 1,
wherein the second processor of the mobile information terminal is further configured to analyze the ultrasound image to perform measurement on a measurement target in the ultrasound image.

9. The ultrasound system according to claim 1, further comprising:
a server device that is connected to the mobile information terminal and the external apparatus,
wherein the server device includes fourth processor configured to analyze the ultrasound image to perform measurement on a measurement target in the ultrasound image.

10. The ultrasound system according to claim 1,
wherein the second processor of the mobile information terminal and the third processor of the external apparatus are further configured to perform wireless communication of voice data between each other in two directions.

11. The ultrasound system according to claim 2,
wherein, when the probe freeze instruction is input from the external input device, the second processor of the mobile information terminal is further configured to stop the acquisition of the view image by the camera unit of the mobile information terminal.

12. The ultrasound system according to claim 4,
wherein the mobile information terminal includes a terminal monitor, and
the second processor of the mobile information terminal is further configured to display the ultrasound image and the view image on the terminal monitor.

13. The ultrasound system according to claim 12,
wherein the mobile information terminal includes a terminal input device, and
when the probe freeze instruction is input from the external input device or the terminal input device, guidance on the probe freeze instruction is displayed on the external monitor and the terminal monitor.

14. The ultrasound system according to claim 12,
wherein the mobile information terminal includes a microphone, and
the first processor of the ultrasound probe is further configured to release the stop of the transmission of the ultrasonic wave from the transducer array based on voice input through the microphone.

15. The ultrasound system according to claim 12,
wherein the third processor of the external apparatus is further configured to wirelessly transmit external advice information input through the external input device to the mobile information terminal, and
the second processor of the mobile information terminal is further configured to display the external advice information on the terminal monitor.

16. The ultrasound system according to claim 13,
wherein the external input device has a touch sensor disposed on the external monitor in a superimposed manner,
the terminal input device has a touch sensor disposed on the terminal monitor in a superimposed manner, and
when the probe freeze instruction is input from the external input device or the terminal input device, and any one of a release button displayed on the external monitor, display for guidance on the probe freeze instruction displayed on the external monitor, a release button displayed on the terminal monitor, or display for guidance on the probe freeze instruction displayed on the terminal monitor is touched, the first processor of the ultrasound probe is further configured to release the stop of the transmission of the ultrasonic wave from the transducer array.

17. An ultrasound system comprising:
an ultrasound probe;
a mobile information terminal; and
an external apparatus,
wherein the ultrasound probe includes
a transducer array,
a transmission and reception circuit configured to transmit an ultrasonic wave from the transducer array and generate a sound ray signal based on a reception signal acquired by the transducer array,
a first processor configured to
generate an ultrasound image based on the sound ray signal generated by the transmission and reception circuit,
give a time stamp representing a time at which the ultrasound image is generated to the ultrasound image, and
wirelessly transmit the ultrasound image to the mobile information terminal,
the mobile information terminal includes
a camera unit configured to
acquire a view image obtained by imaging a scanning point of the ultrasound probe in a subject, and
give a time stamp representing a time at which the view image is generated to the view image, and
a second processor configured to
synchronize the ultrasound image and the view image captured at the same timing with each other by referring to the time stamp given to the ultrasound image wirelessly transmitted from the first processor and the time stamp given to the view image acquired by the camera unit, and
wirelessly transmit the ultrasound image and the view image synchronized with each other to the external apparatus,
the external apparatus includes
an external monitor,
a third processor configured to
wirelessly communicate with at least the second processor,
display the ultrasound image and the view image synchronized with each other by the second processor and wirelessly transmitted from the second processor on the external monitor, and
an external input device, and
wherein, when a probe freeze instruction is input from the external input device,
the third processor of the external apparatus is further configured to transmit the probe freeze instruction to the first processor via the second processor,
the first processor of the ultrasound probe is further configured to stop the transmission of the ultrasonic wave from the transducer array by the transmission and reception circuit of the ultrasound probe,
the second processor is further configured to stop the acquisition of the view image by the camera unit of the mobile information terminal,
the second processor is further configured to analyze the ultrasound image to perform measurement on a measurement target in the ultrasound image, and
each of the mobile information terminal and the external apparatus further includes a microphone and a speaker, and the second processor of the mobile information terminal and the third processor of the external apparatus are further configured to perform wireless communication of voice data between each other in two directions.

* * * * *